United States Patent [19]
Lathe et al.

[11] Patent Number: 5,976,850
[45] Date of Patent: Nov. 2, 1999

[54] HIPPOCAMPUS-ASSOCIATED PROTEINS; DNA SEQUENCES CODING THEREFOR AND USES THEREOF

[75] Inventors: Richard Lathe; Kenneth Andrew Rose, both of Edinburgh, United Kingdom; Genevieve Stapleton, Seattle, Wash.

[73] Assignee: University of Edinburgh, Edinburgh, United Kingdom

[21] Appl. No.: 08/845,161

[22] Filed: Apr. 21, 1997

[30]    Foreign Application Priority Data

Oct. 19, 1994 [GB] United Kingdom .................. 9421093
Oct. 18, 1995 [GB] United Kingdom .... PCT/GB95/02465

[51] Int. Cl.$^6$ .............................. C12N 9/02; C12P 21/06; C07H 17/00
[52] U.S. Cl. ...................... 435/189; 435/69.1; 536/23.1; 536/24.3; 536/23.2
[58] Field of Search ................................ 536/23.1, 24.3; 435/69.1, 189

[56]    References Cited

FOREIGN PATENT DOCUMENTS 0 608 840 A2   4/1995   European Pat. Off. .

OTHER PUBLICATIONS

Noshiro et al. "Molecular cloning and sequence analysis of cDNA encoding . . . " FEBS LETT., vol. 268 No. 1, Jul. 1990, pp. 137–140.
Noshiro et al. "Molecular cloning for cholesterol 7–alpha–hydroxylase . . . "FEBS LETT., vol. 257, No. 1, Oct. 1989, pp. 97–100.
Karam et al. "Polymorphisms of human cholesterol . . . " Biochem. Biophys. Res. Commun., vol. 185 No. 2, 1992, pp. 588–595.
Chung et al. "Structure of a bovine gene for P450c21 . . . " Proc. Natl. Acad. Sci., vol. 83, Jun. 1986, pp. 4243–4247.
Bahmre et al. "Microsomal cytochrome P450 . . . " Biochem. Pharmacology, vol. 44 No. 6, Sep. 25, 1992, pp. 1223–1225.
Theron et al. "Evidence that estradiol–2/4–hydroxlase . . . " J. Steroid Biochem., vol. 23 No. 6a, Nov. 1985, pp. 919–927.
Volk. "Mapping of phenytoin–inducible cytochrome p450 . . . " Neuroscience, vol. 42 No. 1, 1991, pp. 215–235.
Anandatheerthavarada et al. "Rat brain cytochromes P–450 . . . " Brain Res., vol. 536 No. 1–2, Dec. 1990, pp. 339–343.
Stryer et al. 1981. Biochemistry 2nd Ed. W.H. Freeman and Company, San Francisco pp. 629.

Primary Examiner—Karen Cochrane Carlson
Attorney, Agent, or Firm—Nixon & Vanderhye

[57]    ABSTRACT

This invention provides novel hippocampus-associated proteins and DNA sequences coding therefor. In an investigation of hippocampus-associated proteins by differential screening of a rat hippocampus cDNA library, a cDNA species encoding a novel protein designated Hct-1 was isolated and shown to be a to cytochromes P450. The use of hybridization probes based on the rat Hct-1 sequence has led to the identification of homologues in other mammalian species.

13 Claims, 24 Drawing Sheets

Fig. 1B-1

```
A  L  E  Y  Q  Y  V  M  K  N  P  K  Q  L  S  F  E  K  F  S
GCCTTGGAGTACCAGTATGTAATGAAAAACCCAAAACAATTAAGCTTTGAGAAGTTCAGC    60
 R  R  L  S  A  K  A  F  S  V  K  K  L  L  T  N  D  D  L  S
CGAAGATTATCAGGCGAAAGCCTTCTCTGTCAAGAAGCTGCTAACTAATGACGACCTTAGC  120
 N  D  I  H  R  G  Y  L  L  L  Q  G  K  S  L  D  G  L  L  E
AATGACATTCACAGAGGCTATCTTCTTTTACAAGGCAAATCTCTGGATGGTCTTCTGGAA   180
 T  M  I  Q  E  V  K  E  I  F  E  S  R  L  L  K  L  T  D  W
ACCATGATCCAAGAAGTAAAAGAAATATTTGAGTCCAGACTGCTAAAACTCACAGATTGG   240
 N  T  A  R  V  F  D  F  C  S  S  L  V  F  E  I  T  F  T  T
AATACAGCAAGAGTATTTGATTTCTGTAGTTCACTGGTATTTGAAATCACATTACAACT    300
 I  Y  G  K  I  L  A  A  N  K  K  Q  I  I  S  E  L  R  D  D
ATATATGGAAAAATCTTGCTGCTAACAAAAAACAAATTATCAGTGAGCTGAGGGATGAT   360
 F  L  K  F  D  D  H  F  P  Y  L  V  S  D  I  P  I  Q  L  L
TTTTTAAAATTTGATGACCATTTCCCATACTTAGTATCTGACATACCTATTCAGCTTCTA  420
 R  N  A  E  F  M  Q  K  K  I  K  C  L  T  P  E  K  V  A
AGAAATGCAGAATTTATGCAGAAGAAAATTAAATGTCTCACCACCAGAAAAGTAGCT     480
 Q  M  Q  R  R  S  E  I  V  Q  E  R  Q  E  M  L  K  K  Y  Y
CAGATGCAAAGACGGTCAGAATTTGTTCAGGAGAGGCAGGAGATGCTGAAAAATACTAC   560
 G  H  E  E  F  E  I  G  A  H  H  L  G  L  L  W  A  S  L  A
GGGCATGAAGAGTTTGAAATAGGAGCACATCATCTTGGCTTCTGGCTTCCTCCTAGCA    600
 N  T  I  P  A  M  F  W  A  M  Y  Y  L  L  Q  H  P  E  A  M
AACACCATTCCAGCTATGTTCTGGGCAATGTATTATCTTCTTCAGCATCCAGAAGCTATG  660
 E  V  L  R  D  E  I  D  S  F  L  Q  S  T  G  Q  K  K  G  P
GAAGTCCTGCGTGACGAAATTGACAGCTTCCTGCAGTCAACAGGTCAAAAGAAAGGACCT  720
```

Fig. 1B-2

```
          G   I   S   V   H   F   T   R   E   Q   L   D   S   L   V   C   L   E   S   A
     GGAATTCTGTCCACTTCCACCAGAGAACAATTGGACAGCTTGTCTGCCTGGAAAGCGCT    780
      I   L   E   V   L   R   L   C   S   Y   S   S   I   R   E   V   Q   E   D
     ATTCTTGAGGTTCTGAGGTTGTGCTCCTACTCCAGCATCATCCGTGAAGTCAAGAGGAT    840
      M   D   F   S   S   E   S   R   S   Y   R   L   R   K   G   D   F   V   A   V
     ATGGATTTCAGCTCAGAGAGTAGGAGCTACCGTCTGCGAAGGAGACTTTGTAGCTGTC    900
      F   P   P   M   H   N   D   P   E   V   F   D   A   P   K   D   F   R   F
     TTTCCTCCAATGATACACAATGACCCAGAGTCTTCGATGCTCCAAAGGACTTTAGTTT    960
      D   R   F   V   E   D   G   K   K   T   F   F   K   G   G   K   K   L
     GATCGCTTCGTAGAAGATGGTAAGAAGACATTTTTCAAGGAGGAAAAAGCTG        1020
      K   S   Y   I   P   F   G   L   G   T   S   K   C   P   G   R   Y   F   A
     AAGAGTTACATATACCATTTGGAGACTTCCAAGTGTCCAGGCAGATACTTTGCA        1080
      I   N   E   M   K   L   V   I   H   L   T   Y   F   D   L   E   V   I
     ATTAATGAAATGAAGCTACTAGTGATTATACTTTTAACTTATTTGATTTAGAAGTCATT    1140
      D   T   K   P   I   G   L   N   H   S   R   M   F   L   G   I   Q   H   P   D
     GACACTAAGCCTATAGGACTAAACCACAGTCGCATGTTTCTGGGCATTCAGCATCCAGAC    1200
      S   D   I   S   F   R   Y   K   A   K   S   W   R   S   ***
     TCTGACATCTCATTTAGGTACAAGGCAAAATCTTGGAGATCCTGAAAGGGTGGCAGAGAA    1260
     GCTTAGCGGAATAAGGCTGCACATGCTCTGAGCTCTGTGATTGCTGTACTCCCAAATGCA    1320
     GCCACTATTCTTGTTGTTAGAAATGGCAAATTTTATTTGATTGGATCCATCCAGTT    1380
     TGTTTTGGGTCACAAACCTGTCATAAAATAAGCGCTGTCATGTGTaaaaaatgtca    1440
```

Fig. 1B-3

```
tggcaatcattcaggataaggtaaaataacgtttcaagtttgtactactatgatttt 1500
tatcattgtagtgaatgtgctttttccagtaaatttgcgccagggtgatttttttta 1560
attactgaaatccctctaatatcggttttatgtgctgccagaaagtgtgccatcaatgga 1620
cagtataacaatttccagagagaagggagaaattaagcccccatgagttacgctg 1680
tataaaattgtctcttcaactataatatcaataatgtctatatcaccaggttacctttg 1740
cattaaatcgagttttgcaaaag 1763
```

```
ggcaggcacagcctctggtctaagagagagggcactgtgcagaagccatcgctccctaC         60
                                M  Q  G  A  T  T  L  D  A  A  S  P  G  P     14
AGAGCCGCCAGCTCGGGATGCAGGGAGCCACGACCCTAGACGCCGCCAGTCCGCCAGGGC        120
 L  A  L  L  G  L  L  F  A  A  T  L  L  L  S  A  L  F  L  L          34
CTCTCGCCCTCCTAGCCCTTCTCTTTGCCGCCACCTTACTGCTCTCGGCCCTGTTCCTCC        180
 T  R  T  R  R  P  R  E  P  P  L  I  K  G  W  L  P  Y  L            54
TCACCCGGACGCGCCAGGCCCTCGAACCCCCTGAACACCCGTGCTTCCTTATC               240
 G  M  A  L  K  F  F  K  D  P  L  T  F  L  K  T  L  Q  R  Q          74
TGGGCATGGCCCTGAAATTCTTTAAGGATCCGTTAACTTTCTTGAAAACTCTTCAAGGC        300
 H  G  D  T  F  T  V  F  L  V  G  K  Y  I  T  F  V  L  N  P         94
AACATGGTGACACTTTCACTGTCTCCTTGTGGGAAGTATATAACATTTGTCTGAACC          360
 F  Q  Y  V  T  K  N  P  K  Q  L  S  F  Q  K  F  S  S              114
CTTTCCAGTACCAGTATATGTAACGAAAAACCCAAAACAATTAAGCTTTCAGAAGTTCAGCA    420
```

Fig. 3B-2

```
        R   L   S   A   K   A   F   S   V   K   K   L   L   T   D   D   D   L   N   E          134
      GCCGATTATCAGCGAAAGCCTTCTCTGTAAAGAAGCTGCTTACTGATGACGACCTTAATG                                480
        D   V   H   R   A   Y   L   L   L   Q   G   K   P   L   D   A   L   L   E   T          154
      AAGACGTTCACAGAGCCTATCTACTTCTACAGGCAAACCTTTGGATGCTCTTCTGAAA                                  540
        M   I   Q   E   V   K   E   L   F   E   S   Q   L   L   K   I   T   D   W   N          174
      CTATGATCCAAGAAGTAAAAGAATTATTTGAGTCCCAACTGCTAAAATCACAGATTGGA                                 600
        T   E   R   I   F   A   F   C   G   S   L   V   F   E   I   T   F   A   T   L          194
      ACACAGAAAGAATATTTGCATTCTGTGGCTCACTGGTATTTGAGATCACATTTGCGACTC                                660
        Y   G   K   I   L   A   G   N   K   K   Q   I   I   S   E   L   R   D   D   F          214
      TATATGGAAAAATTCTTGCTGGTAACAAGAAACAAATTATCAGTGAGCTAAGGGATGATT                                720
        F   K   F   D   D   M   F   P   Y   L   V   S   D   I   P   I   Q   L   L   R          234
      TTTTTAAATTTGATGACATGTTCCCATACTTAGTATCTGACATTCCTATTCAGTTCTAA                                 780
        N   E   E   S   M   Q   K   K   I   I   K   C   L   T   S   E   K   V   A   Q          254
      GAAATGAAGAATCTATGCAGAAGAAAATTATAAAATGCCTCACATCAGAAAAGTAGCTC                                 840
        M   Q   G   Q   S   K   I   V   Q   E   S   Q   D   L   L   K   R   Y   Y   R          274
      AGATGCAAGGACAGTCAAAAATTGTTCAGGAAGCCAAGATCTGCTGAAAAGATACTATA                                 900
        H   D   D   P   E   I   G   A   H   H   L   G   F   L   W   A   S   L   A   N          294
      GGCATGACGATTCTGAAATAGGAGCACATCATCTTGGCTTTCTCTGGGCCTCTCTAGCAA                                960
        T   I   P   A   M   F   W   A   M   Y   Y   I   L   R   H   P   E   A   M   E          314
      ACACCATTCCAGCTATGTTCTGGGCAATGTATTATATTCTTCGGCATCCTGAAGCTATGG                                1020
        A   L   R   D   E   I   D   S   F   L   Q   S   T   G   Q   K   K   G   P   G          334
      AAGCCCTGCGTGACGAAATTGACAGTTTCCTGCAGTCAACAGGTCAAAAGAAAGGGCCTG                                1080
```

Fig. 3B-3

```
       I  S  V  H  F  T  R  E  Q  L  D  S  L  V  C  L  E  S  T  I    354
GAATTCAGTCCACTTCACCAGAGAACAATTGGACAGCTTGGTCTGCCTGGAAAGCACTA          1140
 L  E  V  L  R  L  C  S  Y  S  S  I  I  R  E  V  Q  E  D  M          374
TTCTTGAGGTTCTGAGGCTGTGCTCATACTCCAGCATCATCCGAGAAGTGCAGGAGGATA         1200
 N  L  S  L  E  S  K  S  F  S  L  R  K  G  D  F  V  A  L  F          394
TGAATTCAGCTTAGAGAGTAAGAGTTTCTCTGCGGAAAGGAGATTTGTAGCCCTCT             1260
 P  P  L  I  H  N  D  P  E  I  F  D  A  P  K  E  F  R  F  D          414
TTCCTCCACTCATACACAATGACCCGGAAATCTTCGATGCTCCAAAGGAATTTAGGTTCG         1320
 R  F  I  E  D  G  K  K  K  S  T  F  F  K  G  G  K  R  L  K          434
ATCGGTTCATAGAAGATGGTAAGAAGAAGAAAAGCACGTTTTTCAAGGAGGAAGAGGCTGA        1380
 T  Y  V  M  P  F  G  L  G  T  S  K  C  P  G  R  Y  F  A  V          454
AGACTTACGTTATGCCTTTTGGACTCGGAACAAGCAAATGTCCAGGAGATATTTGCAG           1440
 N  E  M  K  L  L  I  E  L  L  T  Y  F  D  L  E  I  I  D             474
TGAACGAAATGAAGCTACTGCTTTAACTTATTTGATTTAGAATTATCG                     1500
 R  K  P  I  G  L  N  H  S  R  M  F  L  G  I  Q  H  P  D  S          494
ACAGGAAGCCTATAGGGCTAAATCACAGTCGGATGTTTTAGGTATTCAGCACCCCGATT          1560
 A  V  S  F  R  Y  K  A  K  S  W  R  S  * * *                        507
CTGCCGGTCCCTTAGGTACAAAGCAAAATCTTGGAGAAGCTGAAAGTGTGGCAGAGAAG          1620

CTTTGCAGAGTAAGGCTGCATGTGCTGAGCTCCGTGATTGGTGCACTCCCCAAATGCA           1680

ACCGCTACTCTTGTTTGAAAATGGCAAATTTATATTGGTTGAGATCAATCCAGTTGGTT          1740
```

Fig. 3B-4

TTGGGTCACAAACCTGTCATAAAATAAAGCAGTGTGATGGtttaaaaatgtcatggca 1800 atcatttcaggataaaataacatttcaagtttgtactactatgattttatca 1860 tttgtagtgaatgtgctttt 1880

Fig. 4A-1

```
MoHct-1    1   MQGATTLDAASPGPLALLGLLFAATLLLSALFLLTRRTRRPREPPLIKGW            50
                                       |  |       | |    |      ||||
HuCYP7     1   M--MTTSLIWGIAIAACCCL------WLILGIRRRQTG-EPPLENGL              38

51   GWLPYLGMALKFFKDPLTFLKTLQRQHGDTFTVFLVGKYITFVLNPFQYQYVTKNPKQLSFQKF  112
               || ||||| |  ||  | |||||||  | | | ||||| |      |  |||    | |||
HuCYP7    39   GLIPYLGCALQFGANPLEFLRANQRKHGHVFTCKLMGKYVHFITNPLSYHKVLCHGKYFDWKKF  100

113   SSRLSAKAFSVKKLLT-DDDLNEDVHRAYL-LLQGKPLDALLETMI---QEVKELFESQLLKIT  171
                || |||||   |||| ||| | |  | || ||| | |  | ||||   || ||||  ||  |
         101   HFATSAKAFGHRSIDPMDGNTTENINDTFIKTLQGHALNSLTESMMENLQRIMRPPVSSNSKTA  164

172   DWNTERIFAFCGSLVFEITFATLYGKILA---GNKKQIISELRDDFFKFDDM-FPYLVSDIPIQ  231
                |||| ||||  | | |  ||   |||||   ||||| | || | | ||||   | || || |
         165   AWVTEGMYSFCYRVMFEAGYLTIFGRDLTRRDTQKAHILNNL--DNFKQFDKVFPALVAGLPIH  226

232   LLRNEESMQKKIIKCLTSEKVAQMQGQSKIVQESQDLLKRYYRHDDPEIGAHHLGFLWASLANT  295
                  | | |||| | | |||| ||  |||||||   || || ||||||||| ||||||| |  *
         227   MFRTAHNAREKLAESLRHENLQKRESISELISLRMFLNDTLSTFDDLEKAKTHLVVLWASQANT  290

296   IPAMFWAMYYILRHPEAMEALRDEIDSFLQSTGQKKG-PGISVHFTREQLDSLVCLESTILEVL  358
                ||  | | |  |||||| |    || |  || |||  ||| ||||| ||   | |   |  |
         291   IPATFWSLFQMIRNPEAMKAATEEVKRTLENAGQKVSLEGNPICLSQAELNDLPVLNSIIKESL  354
                                                                C

359   RLCSYSSIIREVQEDMNLSLESKSFSLRKGDFVALFPPLIHNDPEIFDAPKEFRFDRF-IEDGK  421
                | || || |   ||   | || |  | || | |||| |||| ||| |||| | || | ||||
         355   RLSSASLNIRTAKEDFTLHLEDGSYNIRKDSIIALYPQLMHLDPEIYPDPLTFKYDRYLDENGK  418
```

```
                                                          B
422 KKSTFFKGGKRLKTYVMPFGLGTSKCPGRYFAVNEMKLLLIELLTYFDLEIID--RKPIGLNHS  483
         |  |  |   | |    |||   ||||     |   |  | |  ||      |   |  |
419 TKTTFYCNGLKLKYYYMPFGSGATICPGRLFAIHEIKQFLIMLSYFELELIEGQAKCPPLDQS   482

484 RMFLGIQHPDSAVSFRYKAKSWRS* 507
    |  |   |   |   |  |  |
483 RAGLGILPPLNDIEFKYKFKHL*   504
```

|         |   |   |   |   |   |   |   |   |   |   |   |   |   |   |
|---------|---|---|---|---|---|---|---|---|---|---|---|---|---|---|
| MoHct-1 | F | G | L | G | T | S | K | C | P | G | R | Y | F | A |
| HuCYP7  | F | G | S | G | A | T | I | C | P | G | R | L | F | A |
| CYP17   | F | G | A | G | P | R | S | C | V | G | E | M | L | A |
| CYP11B  | F | G | F | G | M | R | Q | C | L | G | R | R | L | A |
| CYP21B  | F | G | C | G | A | R | V | C | L | G | E | P | V | A |
| CYP11A1 | F | G | W | G | V | R | Q | C | L | G | R | R | I | A |
| CYP27   | F | G | Y | G | V | R | A | C | L | G | R | R | I | A |

Fig. 4C

|         |   |   |   |   |   |   |   |   |   |   |   |   |   |   |   |
|---------|---|---|---|---|---|---|---|---|---|---|---|---|---|---|---|
| MoHct-1 | V | C | L | E | S | T | I | L | E | V | L | R | L | C | S |
| HuCYP7  | P | V | L | N | S | I | K | E | S | L | R | L | S | S |   |
| CYP17   | V | L | L | E | H | T | I | R | E | V | L | R | I | R | P |
| CYP11B  | P | L | L | R | A | A | L | K | E | T | L | R | L | Y | P |
| CYP21B  | P | L | L | N | A | T | I | A | E | V | L | R | L | P | V |
| CYP11A1 | P | L | L | K | A | S | I | K | E | T | L | R | L | H | P |
| CYP27   | P | L | L | K | A | V | L | K | E | T | L | R | L | Y | P |

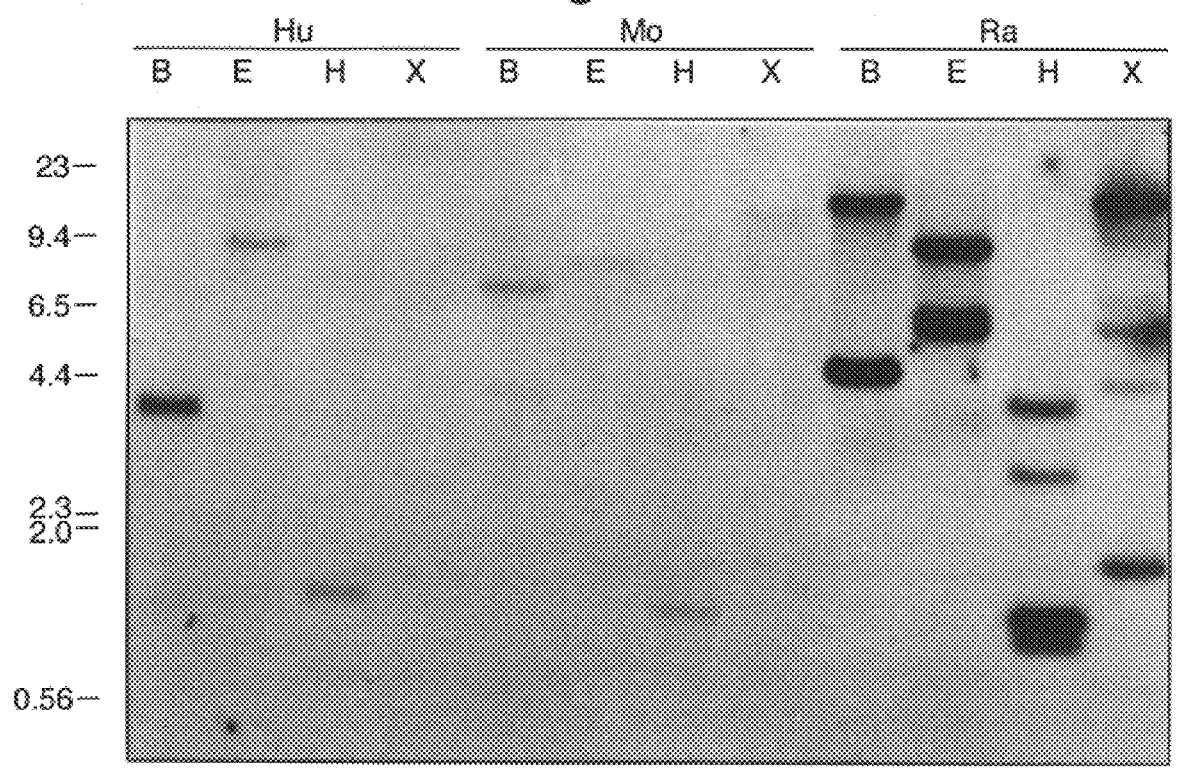

Fig. 9-1

Partial nucleotide sequence of human genomic Hct-1 (CYP7B1) and the encoded polypeptide

```
ggatccaaccaagtttccagatcttataaatgtggtgaatggtgaatgacttcctgaaga      60 atggatgaatggatgtgttctagtttggaatcctgtgtcagtcacaagtcaatatgtgac     120 cttgaacatgttattaaatctcccacatccataaaagtgaaaatgctggcattagtggat     180 ttttgccagtgttgaattagacatttatttgtgagtacctgctccatacagtatggtcat     240 ttatttgagttaaaattgttgtatttgaacaaaactcagatgacacctaagcatgaaaaa     300
                            intron 2
gctctttatgaagtataaatactcagaaatggaatggcatgttgccaatttgttttctgc     360 tttattgagggaaatatatgagaagtatttaagtcaggggattatgaggaatatttaaag     420 gata(~~190nt~)tctagagtgttttccaccatctttcaaaggaaacatgtagtgtacc     680 ttcgaatgaaatggatttgtattaaacttttgccttagttatagggtctttctaattt      740 ttgattaacatatttttttaatttgtggtgtttatttctgtttttattaacaaacgaact    800

GlyLysTyrIleThrPheIleProGlyPro
catatgctcctctctcttttttttttttctGGAAAGTACATAACATTTATACCTGGACCC     860

PheGlnTyrGlnLeuValIleLysAsnHisLysAsnLeuSerPheArgValSerSerAsn
TTCCAGTACCAGCTAGTGATAAAAAATCATAAACAATTAAGCTTTCGAGTATCTTCTAAT     920

LysLeuSerGluLysAlaPheSerIleSerGlnLeuGlnLysAsnHisAspMetAsnAsp
AAATTATCAGAGAAAGCATTTAGCATCAGTCAGTTGCAAAAAAATCATGACATGAATGAT     980

GluLeuHisLeuCysTyrGlnPheLeuGlnGlyLysLysSerLeuAspIleLeuLeuGluSer
GAGCTTCACCTCTGCTATCAATTTTTGCAAGGCAAATCTTTGGACATACTCTTGGAAAGC    1040
                            exon 3
MetMetGlnAsnLeuLysGlnValPheGluProGlnLeuLeuLysThrThrSerTrpAsp
ATGATGCAGAATCTAAAACAAGTTTTTGAACCCCAGCTGTTAAAAACCACAAGTTGGGAC    1100

ThrAlaGluLeuTyrProPheCysSerSerIleIlePheGluIleThrPheThrThrIle
ACGGCAGAACTGTATCCATTCTGCAGCTCAATAATATTTGAGATCACATTTACAACTATA    1160

TyrGlyLysValIleValCysAspAsnAsnLysPheIleSerGluLeuArgAspAspPhe
TATGGAAAAGTTATTGTTTGTGACAACAACAAATTTATTAGTGAGCTAAGAGATGATTTT    1220

LeuLysPheAspAspLysPheAlaTyrLeuValSerAsnIleProIleGluLeuLeyGly
TTAAAATTTGATGACAAGTTTGCATATTTAGTATCCAACATACCCATTGAGCTTCTAGGA    1280

AsnValLysSerIleArgGluKysIleIleLysCysPheSerSerGluLysLeuAlaLys
AATGTCAAGTCTATTAGAGAGAAAATTATAAAATGCTTCTCATCAGAAAAGTTAGCCAAG    1340

MetGlnGlyTrpSerGluValPheGlnSerArgGlnAspAspLeuGluLysTyrTyrVal
ATGCAAGGATGGTCAGAAGTTTTTCAAAGCAGGCAAGATGACCTGGAGAAATATTATGTG    1400
```

Fig. 9-2

```
HisGluAspLeuGluIleGlyA-
CACGAGGACCTTGAAATAGGAGgtaagaacttctgaatgagcacttgcctaaataaaaat 1460 catttacatagacctctgaaataaaaaaagacaaaatggcgaccttgaaaattttttttat 1520 gctctttctaattggctaatgataaatgtttactctgatataacctctataattgatatt 1580 ttttttttgctgaggtggtaaacagatacttaatggtgataatgagaaagcgtataact 1640
                              intron 3
aagctgcatttatccctcttatctcatccccgaccacaccgccccccccatacacattac 1700 attttaaactattctcattaagcagaaaattagacttcagaagcctattggttctcatta 1760 gcatgcagtgatccttggctggtctgtgtcctaacatcttttaattagcacactgcaaat 1820

-laHisHis
ctaatcagtgtaataaacgctattaatcttcctttacacttattttctcccaCACATCAT 1880

PheGlyPheLeuTrpValSerValAlaSerThrIleProThrMetPheTrpAlaThrTyr
TTAGGCTTTCTCTGGGCCTCTGTGGCAAACACTATTCCAACTATGTTCTGGGCAACGTAT 1940
                              exon 4
TyrLeuLeuArgHisProGluAlaMetAlaAlaValArgAspGluIleAspArgLeuLeu
TATCTTCTGCGGCACCCAGAAGCTATGGCAGCAGTGCGTGACGAAATTGACCGTTTGCTG 2000

GlnSerThrGlyGlnLysGluGlySerGlyPheProIleHisLeuThrArgGluGlnLeu
CAGTCAACAGGTCAAAAGGAAGGGTCTGGATTTCCCATCCACCTCACCAGAGAACAATTG 2060

AspSerLeuIleCysLeu
GACAGCCTAATCTGCCTAGgtaattatttatctgttatgaagaaagaaggtacctctct 2120 gcaaactcggtttatcactcatagctgtttacaagaggtagaggacacagctgctaattg 2180 acataataactcccatttacatcaattataaattatgtagtttatagccgtagatcatct 2240
                              intron 4
cattgcatgtaaacataaggcctaxgtaattaactgtgxaaxgtatgxaaaaxxctaacc 2300 aaagctt(-~550nt-)cctgactgaacttcttactgccaaagttaaattccataccaat 2960 gagttattctctattctctctgtattgacatttcatctgcggtatcctttagggtacaat 3020 attccaagtttctttagacaaacgcaggaacaaatgttcacatatttctgtttctttatt 3080 cctttgacaagtaggcgagcattttagcctatgttggtctcaaaaaaaatcttttaaata 3140 tgttccaggttctttaatgggaccttt caggagcaaaagtcctcccaggtttggtcaatg 3200 ttcaccctcxgtggccattgaggaaaatgcccxxxxxgttctagagattgttctcacttc 3260 tcaggctaaggcccattgagcaatgccagaaagcatgccttatactagcagtcaatttgg 3320 aagtttgtagtttgtgtctttagcataggttatcaaataaattttatatttxcttttaaa 3380 aaaatctcaacattactaaaatacaaatatccttttattttctttgcagaattatcggg 3440 gaacaaatccagaaaatttgtgtaaatttcgggtagttgctccacttgatacacagtatt 3500
```

```
tctgcatattgtaatttctatgaagatctaggttgcatttcccatacattcaagcagttt  3560
ccattgcatttttatgaataagatgacgcatactgggaagtaaggcaaatacactaaaag  3620
gaatatgtgtttgtattctgtatagttattactcttaaaaaaagtagttgtaattcatcc  3680
actcttttactttcaacttttgctattaaaaaatcatttttaaatttcagtattaaag    3740
cagaaacatttaaatttattagaccagaaaaataacagattctagaactataatttgaat  3800
ccatttaagcccatagctagagctagagattttcactattggatcc  3846
```

Comparison of human and mouse Hct-1 (Cyp7b1) sequences (exons III and IV)

human
```
G K Y I T F I P G P F Q Y Q L V I K N H K Q L S F R V S S N
G K Y I T F V L N P F Q Y Q Y V T K N P K Q L S F Q K F S S
```
mouse

```
K L S E K A F S I S Q L Q K N H D M N D E L H L C Y Q F L Q
R L S A K A F S V K K L L T D D D L N E D V H R A Y L L L Q

G K S L D I L L E S M M Q N L K Q V F E P Q L L K T T S W D
G K P L D A L L E T M I Q E V K E L F E S Q L L K I T D W N

T A E L Y P F C S S I I F E I T F T T I Y G K V I V C D N N
T E R I F A F C G S L V F E I T F A T L Y G K I L A G N K K

K F I S E L R D D F L K F D D K F A Y L V S N I P I E L L G
Q I I S E L R D D F F K F D D M F P Y L V S D I P I Q L L R

N V K S I R E K I I K C F S S E K L A K M Q G W S E V F Q S
N E E S M Q K K I I K C L T S E K V A Q M Q G Q S K I V Q E
```

◄-----exon III - exon IV-----►
```
R Q D D L E K Y Y V H E D L E I G - A H H F G F L W V S V A
S Q D L L K R Y Y R H D D S E I G - A H H L G F L W A S L A S T I P T M F W A T Y Y L L R H P E A M A A V R D E I D R L
N T I P A M F W A M Y Y I L R H P E A M E A L R D E I D S F L Q S T G Q K E G S G F P I H L T R E Q L D S L I C L
L Q S T G Q K K G P G I S V H F T R E Q L D S L V C L
```

Shared identity = 163/266 residues; 61% identity (74% over exon IV)

Fig. 11A

Kozak sequences in mRNAs for steroidogenic P450's

Nucleotide sequences conforming are in bold; sequences diverging from the consensus are underlined consensus yyRyy ATG R (a)
| | | | | |
|---|---|---|---|---|
| BovCYP21 | - | CTCC<u>A</u>GCC | ATG | GTCCTCG |
| HumCYP21 | - | GTCTCGCC | ATG | <u>C</u>TGCTCC |
| HumCYP17 | - | CAGCCACC | ATG | <u>T</u>GGGAGC |
| MusCYP7B | - | TCGTCG<u>GG</u> | ATG | <u>C</u>AGGGAG |
| HumCYP7 | - | TTTGCA<u>AA</u> | ATG | ATGACCA |
| RatCYP7 | - | TTTGCA<u>AA</u> | ATG | ATGACTA |
| MusCYP7 | - | TTTGCA<u>AA</u> | ATG | ATGAGCA |
| RabCYP27 | - | TCGGATCC | ATG | GCTGCGC |
| RatCYP27 | - | CACGATCT | ATG | GCTGTGT |

Sequence selected for the mouse Hct-1 coding sequence in vaccinia virus

MusCYP7B* - TCGCCACC ATG CAGGGAG

Fig. 11B

B. Mutagenesis of the 5' end of the mouse Hct-1 cDNA to create a near-consensus translation initiation region surrounding the ATG (AUG)

(i). Sequence surrounding the initiating ATG and the translation termination site

```
           M  Q  G  A  T  T  L  D  ---  K  S  W  R  S  ***
AGAGCCGCCAGCTCGTCGGGATGCAGGGAGCCACGACCCTAG --- AAATCTTGGAGAAGCTGAAAGTGTGGCAGAGAAG
```

(ii). PCR primers for modification of the translation initiation site and 3' truncation of the cDNA clone

```
           GGCCCTCGAGCCACCATGCAGGGAGCCACG →
           ||||||||||||||||||||||||||||||                              AGAACCCTCTTCGACTCTTAAGCCGG ←
AGAGCCGCCAGCTCGTCGGGATGCAGGGAGCCACGACCCTAG --- AAATCTTGGAGAAGCTGAAAGTGTGGCAGAGAAG
                                                ||||||||||||||||||||||||||
                                                → AGAACCCTCTTCGACTCTTAAGCCGG
```

5' PRIMER    GGCCCTCGAGCCACCATGCAGGGAGCCACG

3' PRIMER    GGCCGAATTCTCAGCTTCTCCAAGAA

Yeast expression vectors containing the mouse
Hct-1 coding sequence

Clone pMA Not 146 (A) contains the mouse Hct-1 cDNA clone 35; pMA Not 147 (B) contains cDNA clone 40.

HIPPOCAMPUS-ASSOCIATED PROTEINS; DNA SEQUENCES CODING THEREFOR AND USES THEREOF

This invention relates to novel hippocampus-associated proteins, to DNA sequences coding therefor, to uses thereof and to antibodies to said proteins. The novel hippocampus-associated proteins are believed to be of the cytochrome P450 class.

BACKGROUND TO THE INVENTION

The identification of hippocampus-associated proteins and the isolation of cDNA molecules coding therefor is important in the field of neurophysiology. Thus, for example, such proteins are believed to be associated with memory functions and abnormalities in these proteins, including abnormal levels of expression and the formation of modified or mutated protein is considered to be associated with pathological conditions associated with memory impairment. The isolation of novel hippocampus-associated proteins and the associated DNA sequences coding therefor is consequently of considerable importance.

The present invention arose out of our investigation of hippocampus-associated proteins by differential screening of a rat hippocampus cDNA library. A cDNA species encoding a novel protein which we have designated Hct-1 was isolated and shown to be related to cytochromes of the P450 class.

The use of hybridization probes based on the rat Hct-1 sequence has led to the identification of homologues in other mammalian species, specifically mouse and human.

Cytochromes P450 are a diverse group of heme-containing mono-oxygenases (termed CYP's; see Nelson et al., DNA Cell Biol. (1993) 12, 1–51) that catalyse a variety of oxidative conversions, notably of steroids but also of fatty acids and xenobiotics. While CYP's are most abundantly expressed in the testis, ovary, placenta, adrenal and liver, it is becoming clear that the brain is a further site of CYP expression. Several CYP activities or mRNA's have been reported in the nervous system but these are predominantly of types metabolizing fatty acids and xenobiotics (subclasses CYP2C, 2D, 2E and 4). However, primary rat brain-derived glial cells have the capacity to synthesize pregnenolone and progesterone in vitro. Mellon and Deschepper, Brain Res. (1993), 629, 283–292(9) provided molecular evidence for the presence, in brain, of key steroidogenic enzymes CYP11A1 (scc) and CYP11B1 (11β) but failed to detect CYP17 (c17) or CYP11B2 (AS). Although CYP21A1 (c21) activity is reported to be present in brain, authentic CYP21A1 transcripts were not detected in this tissue.

Interest in steroid metabolism in brain has been fuelled by the finding that adrenal- and brain-derived steroids (neurosteroids) can modulate cognitive function and synaptic plasticity. For instance, pregnenolone and steroids derived from it are reported to have memory enhancing effects in mice. However, the full spectrum of steroid metabolizing CYP's in brain and the biological roles of their metabolites in vivo has not been established.

To investigate such regulation of brain function our studies have focused on the hippocampus, a brain region important in learning and memory. Patients with lesions that include the hippocampus display pronounced deficits in the acquisition of new explicit memories while material encoded long prior to lesion can still be accessed normally. In rat, neurotoxic lesions to the hippocampus lead to a pronounced inability to learn a spatial navigation task, such as the water maze. The role of the hippocampus in learning has been further emphasized by the finding that hippocampal synapses, notably those in region CA1, display a particularly robust form of activity-dependent plasticity known as long term potentiation (LTP). This phenomenon satisfies some of the requirements for a molecular mechanism underlying memory processes—persistence, synapse-specificity and associativity. LTP is thought to be initiated by calcium influx through the NMDA (N-methyl D-aspartate) subclass of receptor activated by the excitatory neurotransmitter, L-glutamate, and occlusion of NMDA receptors in vivo with the competitive antagonist AP5 both blocks LTP and the acquisition of the spatial navigation task.

The induction of LTP is attenuated by simultaneous release of gamma-amino butyric acid (GABA) from inhibitory interneurons: activation of $GABA_A$ receptors antagonizes L-glutamate induced depolarization of the postsynaptic neuron and interplay between the GABA and L-glutamate receptor pathways is thought to modulate the establishment of LTP. Interplay between these two circuits is emphasised by the finding that some aesthetics (e.g. ketamine) act as antagonists of the NMDA receptor while others, such as the steroid aesthetic alfaxolone, are thought to be agonists of the $GABA_A$ receptor. It is of particular note that some naturally occurring steroids, such as pregnenolone sulfate, act as agonists of the $GABA_A$ receptor, while pregnenolone sulfate is also reported to increase NMDA currents. Although neurosteroids principally appear to exert their effects via the $GABA_A$ and NMDA receptors, there have been indications that neurosteroids may also interact with sigma and progesterone receptors.

Despite considerable interest in the action of neuro-active steroids, and possible roles in modulating synaptic plasticity and brain function, little is known of pathways of steroid metabolism in the central nervous system. As part of a study into the molecular biology of the hippocampal formation, and the mechanisms underlying synaptic plasticity, we have sought molecular clones corresponding to mRNA's expressed selectively in the formation. One such cDNA, Hct-1 (for hippocampal transcript), was isolated from a cDNA library prepared from adult rat hippocampus. Sequence analysis has revealed that Hct-1 is a novel cytochrome P450 most closely related to cholesterol- and steroid-metabolizing CYP's but, unlike other CYP's, is predominantly expressed in brain. The present invention provides molecular characterization of Hct-1 coding sequences from rat, mouse and humans, their expression patterns, and discusses the possible role of Hct-1 in steroid metabolism in the central nervous system.

DNA sequences encoding hitherto unknown cytochrome P450 proteins have now been identified and form one aspect of the present invention.

SUMMARY OF THE INVENTION

According to one aspect of the present invention there are thus provided DNA molecules selected from the following:

(a) DNA molecules containing the coding sequence set forth in SEQ ID NO: 1 beginning at nucleotide 22 and ending at nucleotide 1541, (b) DNA molecules containing the coding sequence set forth in SEQ ID NO: 3 beginning at nucleotide 1 and ending at nucleotide 1242, (c) DNA molecules capable of hybridizing with the DNA molecule defined in (a) or (b) under standard hybridization conditions defined as 233 SSC at 65° C.

(d) cytochrome P450-encoding DNA molecules capable of hybridizing with the DNA molecule defined in (a), (b) or (c) under reduced stringency hybridization conditions defined as 6×SSC at 55° C.

Such DNA sequences can represent coding sequences of Hct-1 proteins. The sequences (a) and (b) above represent the mouse and rat Hct-1 gene sequence. Homologous sequences from other vertebrate species, especially mammalian species (including man) fall within the class of DNA molecules represented by (c) or (d).

Thus the present invention further provides a DNA molecule consisting of sequences of the human Hct-1 gene.

These DNA sequences may be selected from the following:

(e) DNA molecules comprising one or more sequences selected from
  (i) the sequence designated "intron 2" in SEQ ID NO:5,
  (ii) the sequence designated "exon 3" in SEQ ID NO:5,
  (iii) the sequence designated "intron 3" in SEQ ID NO:5,
  (iv) the sequence designated "exon 4" in SEQ ID NO:5, and
  (v) the sequence designated "intron 5" in SEQ ID NO:5; and (f) DNA molecules capable of hybridizing with the DNA molecules defined in (e) under standard hybridization conditions defined as 2×SSC at 65° C.

(g) cytochrome P450-encoding DNA molecules capable of hybridizing with the DNA molecule defined in (e) or (f) under reduced stringency hybridization conditions defined as 6×SSC at 55° C.

(h) DNA molecules comprising contiguous pairs of sequences selected from
  (i) the sequence designated "intron 2" in SEQ ID NO:5,
  (ii) the sequence designated "exon 3" in SEQ ID NO:5,
  (iii) the sequence designated "intron 3" in SEQ ID NO:5,
  (iv) the sequence designated "exon 4" in SEQ ID NO:5, and
  (v) the sequence designated "intron 5" in SEQ ID NO:5; and (i) DNA molecules capable of hybridizing with the DNA molecules defined in (h) under standard hybridization conditions defined as 2×SSC at 65° C.

(j) cytochrome P450-encoding DNA molecules capable of hybridizing with the DNA molecule defined in (h) or (i) under reduced stringency hybridization conditions defined as 6×SSC at 55° C.

(k) DNA molecules comprising a contiguous coding sequence consisting of the sequences "exon 3" and "exon 4" in SEQ ID NO:5, and (l) DNA molecules capable of hybridizing with the DNA molecules defined in (k) under standard hybridization conditions defined as 2×SSC at 65° C.

(m) cytochrome P450-encoding DNA molecules capable of hybridizing with the DNA molecule defined in (k) or (l) under reduced stringency hybridization conditions defined as 6×SSC at 55° C.

It will be appreciated that the DNA sequences that include introns (such as the sequences covered by definitions (e) to (j) above), may consist of or be derived from genomic DNA. Those sequences that exclude introns may also be genomic in origin, but typically would consist of or be or be derived from cDNA. Such sequences could be obtained by probing an appropriate library (cDNA or genomic) using hybridisation probes based upon the sequences provided according to the invention, or they could be prepared by chemical synthesis or by ligation of sub-sequences.

The invention further provides DNA molecules encoding an Hct-1 gene-associated sequence coded for by a DNA molecule as defined above, but which differ in sequence from said sequences by virtue of one or more amino acids of said Hct-1 gene-associated sequences being encoded by degenerate codons.

The present invention further provide DNA molecules useful as hybridization probes and consisting of a contiguous sequence of at least 18 nucleotides from the DNA sequence set forth in SEQ ID NOS:1, 3 & 5, respectively.

Such molecules preferably contain at least 24 and more preferably at least 30 nucleotide taken from said sequences.

The aforementioned DNA molecules are useful as hybridization probes for isolating members of gene families and homologous DNA sequences from different species. Thus, for example, a DNA sequence isolated from one rodent species, for example rat, has been used for isolating homologous sequences from another rodent species, for example mouse and from other mammalian species, e.g. primate species such as humans.

Such sequences may be further used for isolating homologous sequences from other mammalian species, for example domestic animals such as cows, horses, sheep and pigs, primates such as chimpanzees, baboons and gibbons.

DNA sequences according to the invention may be used in diagnosis of neuropsychiatric disorders, endocrine disorders, immunological disorders, diseases of cognitive function, neurodegenerative diseases or diseases of cognitive function, for example by assessing the presence of depleted levels of mRNA and/or the presence of mutant or modified DNA molecules. Such sequences include hybridisation probes and PCR primers. The latter generally would be short (e.g. 10 to 25) oligonucleotides in length and would be, capable of hybridising with a DNA molecule as defined above. The invention includes the use of such primers in the detection of genomic or cDNA from a biological sample for the purpose of diagnosis of neuropsychiatric disorders, endocrine disorders, immunological disorders, diseases of cognitive function or neurodegenerative diseases.

The present invention further provides hippocampus-associated proteins as such, encoded by the DNA molecules of the invention.

In particular, there is provided
  (i) the protein designated rat Hct-1 comprising the amino acid sequence set forth in SEQ ID NO:1 or a protein having substantial homology thereto,
  (ii) the protein designated mouse Hct-1 comprising the amino acid sequence set forth in SEQ ID NO:2 or a protein having substantial homology thereto, or
  (iii) the protein designated human Hct-1 comprising the amino acid sequence set forth in SEQ ID NO:5 or a protein having substantial homology thereto.

By "substantial homology" is meant a degree of homology such that at least 50%, preferably at least 60% and most preferably at least 70% of the amino acids match. The invention of course covers related proteins having a higher degree of homology, e.g. at least 80%, at least 90% or more.

The Hct-1 polypeptides may be produced in accordance with the invention by culturing a transformed host and recovering the desired Hct-1 polypeptide, characterised in that the host is transformed with nucleic acid comprising a coding sequence as defined above.

Examples of suitable hosts include yeast, bacterial, insect or mammalian cells. Although vectorless expression may be employed, it is preferred that the nucleic acid used to effect the transformation comprises an expression construct or an expression vector, e.g. a vaccinia virus, a baculovirus vector, a yeast plasmid or integration vector.

The invention further provides antibodies, especially monoclonal antibodies which bind to Hct-1 proteins. These and the proteins of the invention may be employed in the design and/or manufacture of an antagonist to Hct-1 protein for diagnosis and/or treatment of diseases of cognitive function or neurodegenerate diseases. The use of Hct-1-associated promoters in the formation of constructs for use in the creation of transgenic animals is also envisaged according to the invention. The antibodies of the invention may be prepared in conventional manner, i.e. by immunising animal such as rodents or rabbits with purified protein obtained from recombinant yeast, or by immunising with recombinant vaccinia.

Hct-1 proteins provided according to the invention possesses catalytic activity, thus they may be used in industrial processes, to effect a catalytic transformation of a substrate. For example, where the substrate is a steroid, the proteins may be used to catalyse stereospecific transformations, e.g. transformations involving oxygen transfer.

DESCRIPTION OF DRAWINGS (SEE ALSO FIGURE LEGENDS-7 INFRA)

FIG. 1 illustrates (a) a restriction map of clone 1 2 and (b) the complete nucleotide and translation sequence of the 1.4 kb cDNA clone of SEQ ID NOS:1–2, respectively), FIG. 2 illustrates Northern analysis of Hct-1 expression in adult rat and mouse brain, and other tissues, FIG. 3 illustrates (a) restriction maps of clones 35 and 40 and (b) the complete nucleotide and translation sequence of mouse Hct-1 (SEQ ID NO:3–4) cDNA, FIG. 4 illustrates an alignment of mouse Hct-1 (SEQ ID NO:4) with human CYP7 (SEQ ID NO:18) and highlights regions homologous to other steroidogenic P450s (SEQ ID NOS:19–32, respectively), FIG. 5 illustrates an analysis of Hct-1 expression in mouse brain, FIG. 6 illustrates Southern analysis of Hct-1 coding sequences in mouse, rat and human.

FIG. 7 illustrates Southern blot analyses of mouse genomic DNA using (a) a full length mouse Hct-1cDNA clone and (b) rat genomic DNA probed with clone 14.5a, FIG. 8 illustrates a genomic map of mouse Hct-1, FIG. 9 illustrates a partial nucleotide sequence of human genomic Hct-1 (CYP7B1) and the encoded polypeptide (SEQ ID NOS:5–6, respectively), FIG. 10 illustrates an amino acid alignment of mouse Hct-1 (SEQ ID NO:33) and human CYP7 (SEQ ID NO:6), FIG. 11 A illustrates Kozak sequences in mRNAs for steroidogenic P540's (SEQ ID NOS:34–43, respectively), FIG. 11B illustrates mutagenesis of the 5'end of the mouse Hct-1 cDNA to sreate a near-consensus translation initiation region surrounding the ATG (AUG) (various regions of SEQ ID NO:3, as well as SEQ ID NOS:44, 45, 12 & 13, respectively), FIG. 12 illustrates yeast expression vectors containing the mouse Hct-1 coding sequence, and FIG. 13 illustrates a vaccinia expression vectors containing the mouse Hct-1 coding sequence.

DESCRIPTION OF SPECIFIC EMBODIMENTS

Figure 1A:
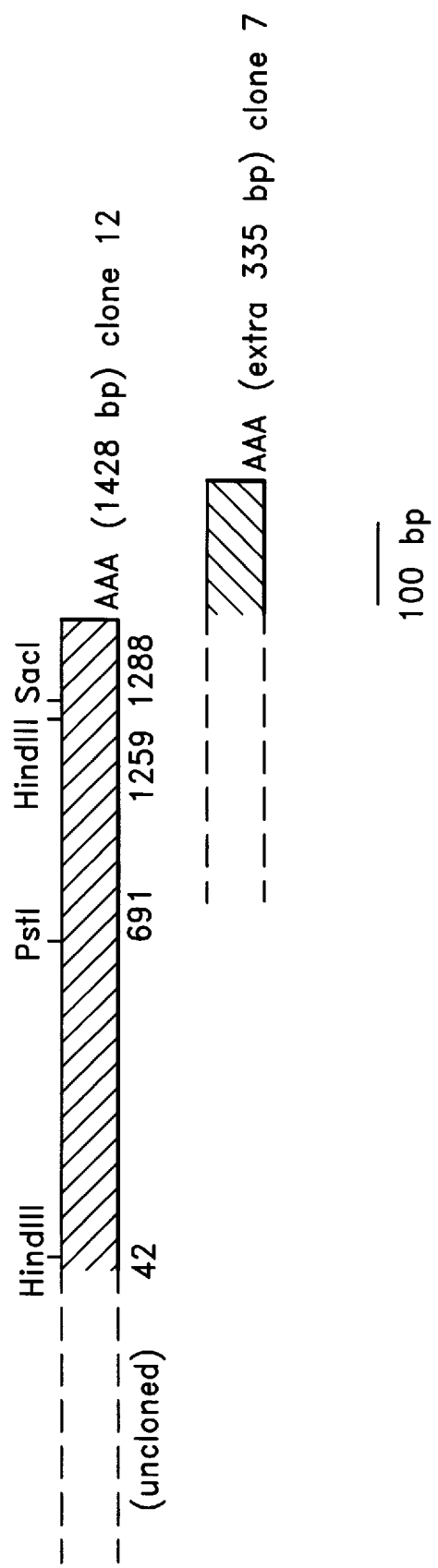

Details of the isolation of hippocampus-associated DNA molecules according to the invention will now be described by way of example:

1. ISOLATION OF GENE ENCODING RAT HCT-1

1.1 Differential screening of a rat hippocampus cDNA library

To identify genes whose expression is enriched in the hippocampal formation we performed a differential hybridization screen of a hippocampal cDNA library. Adult rat hippocampal RNA was reverse transcribed using a oligo-dT-NotI primer, converted to double-stranded cDNA, EcoRI adaptors were attached and the cDNA's were inserted between the EcoRI and NotI sites of a bacteriophage lamda vector.

1.1.1 Preparation of cDNA libraries

Following anaesthesia (sodium pentobarbital) of adult rats (Lister hooded) the hippocampal formation was dissected, including areas CA1–3 and dentate gyrus, subiculum, alvear and fimbrial fibres but excluding fornix and afferent structures such as septum and entorhinal cortex. Remainder of brain was also pooled taking care to exclude hippocampal tissue. Total RNAs were prepared by a standard guanidinium isothiocyanate procedure, centrifugation through a CsCI cushion, and poly-A⁺ mRNA selected by affinity chromatography on oligo-dT cellulose. First strand cDNA synthesis used a NotI adaptor primer

[5-dCAATTCGCGGCCGC(T)₁₅-3']

(SEQ ID NO:7) and Moloney murine leukemia virus (MMLV) reverse transcriptase; second strand synthesis was performed by RNaseH treatment, DNA polymerase I fill-in and ligase treatment. Following the addition of hemi-phosphorylated EcoRI adaptors (5'-dCGACAGCAACGG-3' and 5'-dAATTCCGTTGCTGTCG-3') and cleavage with NotI the cDNA was inserted between the NotI and EcoRI sites of bacteriophage lambda vector lambda-ZAPII (Stratagene).

1.1.2 Differential hybridization screening

Recombinant bacteriophage plaques were transferred in duplicate to Hybond-N membranes (Amersham), denatured (0.5 M NaOH, 1.5 M NaCl, 4 min), renatured (1 M Tris.HCl pH 7.4, 1.5 M NaCl), rinsed, dried and baked (2 h, 80° C.). Hybridization as described (Church et al., Proc. Natl. Acad. Sci. USA (1984), 81 1991–1995) used a radiolabelled probe prepared by MMLV reverse transcriptase copying of polyA⁺ RNA (from either hippocampus or the remainder of brain) into cDNA in the presence of α-³²P-dCTP and unlabelled dGTP, dATP and dTTP according to standard procedures. Following washing and exposure for autoradiography, differentially hybridizing plaques were repurified. Inserts were transferred to a pBluescript vector either by cleavage and ligation or by using in vivo excision using the ExAssist/SOLR system (Stratagene).

Duplicate lifts from 500,000 plaques were screened with radiolabelled cDNA probes prepared by reverse transcription of RNA from either hippocampus (Hi) or 'rest of brain' (RB). Approximately 360 clones gave a substantially stronger hybridization signal with the Hi probe than with the RB probe; 49 were analysed in more depth. In vivo excision was used to transfer the inserts to a plasmid vector for partial DNA sequence studies. Of these, 21 were novel (not presented here); others were known genes whose expression is enriched in hippocampus but not specific to the formation (eg., the rat amyloidogenic protein. Northern analysis was first performed using radiolabelled probes corresponding to the 21 novel sequences. While three (12.10a, 14.5a and 15.13a) identified transcripts specific to the hippocampus, 12.10a and 15.13a both hybridized to additional transcripts whose expression was not restricted to the formation. Clone 14.5a appeared to identify transcripts enriched in hippocampus and was dubbed Hct-1.

1.2 Characterisation of Rat Hct-1

1.2.1 Rat Hct-1 encodes a cytochrome P450

To extend this characterization, the insert of clone 14.5a (300 nt) was used to rescreen the hippocampal cDNA library. 4 positives were identified (clones 14.5a-5, -7, -12 and -13), and the region adjacent to the poly-A tail analysed by DNA sequencing. While clones 5 (0.7 kb) and 12 (1.4 kb) had the same 3' end as the parental clone, clone 7 (0.9 kb) had a different 3' end consistent with utilization of an alternative polyadenylation site. Clone 13 (2.5 kb), however, appeared unrelated to Hct-1 and was dubbed Hct-2.

Clones 12 and 7 were then fully sequenced and the sequences obtained were compared with the database. Significant homology was detected between clone 12 and the human and rat cDNA's encoding cholesterol 7α-hydroxylase, though the sequences are clearly distinct. At the nucleic acid level, the 1428 nt cDNA clone for rat Hct-1 shared 55% identity overan 1100 nt overlap with human cholesterol 7α-hydroxylase (CYP7) and 54% identity over a 1117 nt overlap with rat CYP7. FIG. 1 gives the partial cDNA sequences of rat Hct-1 and the encoded polypeptide.

1.2.2 Hct-1 mRNA expression in rat

Figure 2A:
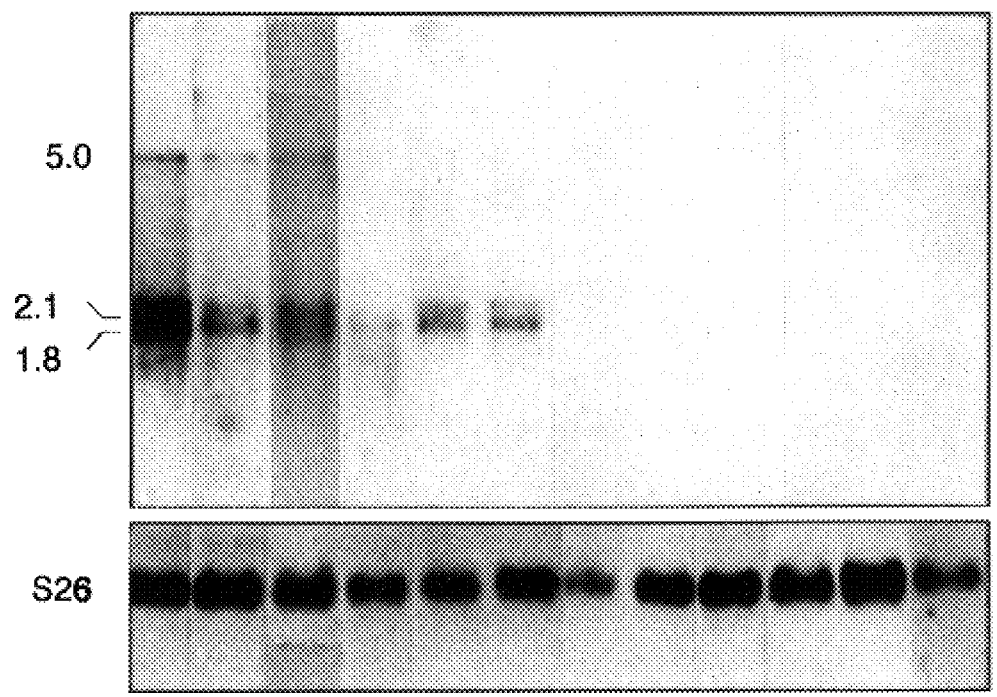

Rat Hct-1 clone 14.5a/12 (1.4 kb) was used to investigate the expression of Hct-1 mRNA in rat brain and other organs. We first performed in situ hybridization to sections of rat brain. While these preliminary experiments did not permit unambiguous localization of Hct-1 transcripts, we confirmed expression in the hippocampus, predominantly in the cell layers of the dentate gyrus, while weaker expression was detected in other hippocampal and brain regions (not presented). Northern analysis was then performed on RNA prepared from different sections of rat brain. In FIG. 2A the Hct-1 probe identifies three transcripts in hippocampus of 5.0, 2.1 and 1.8 kb, with the two smaller transcripts being particularly enriched in hippocampus. The larger transcript was only detectable in brain, while the two smaller transcripts were also present in liver (and, at much lower levels, in kidney) but not in other organs tested including adrenal (not shown), testis, and ovary. In brain, expression was also detected in olfactory bulb and cortex while very low levels were present in cerebellum (FIG. 2A).

1.2.3 Sexual dimorphism of Hct-1 expression in liver but not in brain

Figure 2B:
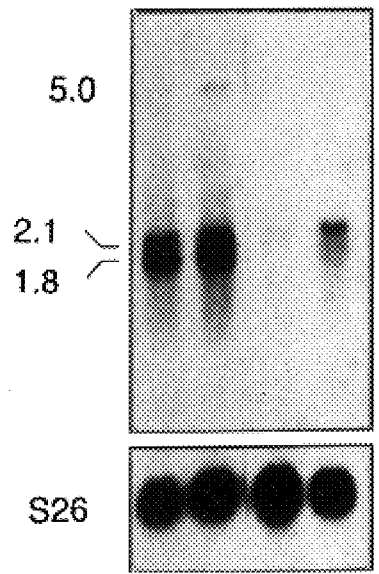

The expression of several CYPS is known to be sexually dimorphic in liver. We therefore inspected liver and brain of male and female rats for the presence of Hct-1 transcripts. In FIG. 2B the Hct-1 probe revealed the 1.8 and 2.1 kb (and 5.0 kb, Hct-2) transcripts in both male and female brain, with the 2.1 kb Hct-1 transcript predominating. Levels of Hct-1 mRNA's in liver were reduced greater than 20-fold over those detected in brain. Furthermore, Hct-1 transcripts were only significant in liver from male animals; expression of Hct-1 in females was barely detectable demonstrating that hepatic expression of Hct-1 is sexually dimorphic.

2. ISOLATION OF MOUSE HCT-1

2.1 Isolation of mouse Hct-1 cDNA clones

A mouse liver cDNA library, established as NotI-EcoRI fragments in a lambda-gt10 vector, was probed using a rat Hct-1 probe. The library was a kind gift of B. Luckow and K. Kästner, Heidelberg.

Because the transcripts identified by the Hct-1 probe (predominantly 1.8 and 2.1 kb) are clearly longer than the longest cDNA clone (1.4 kb) obtained from our rat hippocampus library, we therefore elected to pursue studies with the mouse Hct-1 ortholog. A mouse liver cDNA library was screened using a rat Hct-1 probe and four clones were selected, none containing a poly-A tail. Two (clones 33 and 35, both 1.8 kb) gave identical DNA sequences at both their 5' and 3' ends, and this sequence was approximately 91% similar to rat Hct-1. The remaining two clones, 23 and 40, were also identical to each other and were related to the other clones except for a 5' extension in (59 nt) and a 3' deletion (99 nt). The complete DNA sequences of clones 35 and 40 were therefore determined.

The sequences obtained were identical throughout the region of overlap. The mouse Hct-1 open reading frame (ORF) commences with a methionine at nucleotide 81 (numbering from clone 40) and terminates with a TGA codon at nucleotide 1600, encoding a protein of 507 amino acids (FIG. 3). At the 5' end it is of note that the ATG initiation codon leading the ORF does not correspond to the translation initiation consensus sequence YYAYYATGR. However, the 5' untranslated region cloned is devoid of other possible initiation codons and an in-frame termination triplet (TAA) lies 20 codons upstream of the ATG. The encoded polypeptide sequence aligns well with other cytochrome P450 sequences and we surmise that the ATG at position 81 represents the correct start site for translation. At the 3' end the truncation of clone 40 lies entirely in the non-coding region downstream of the stop codon. Neither clone contained a poly-A tail but both contained a potential polyadenylation sequence (AATAAA) at a position corresponding precisely to that seen in the rat cDNA.

2.2 Structure of mouse Hct-1 polypeptide

As anticipated, nucleotide sequence homology of mouse Hct-1 was highest with human cholesterol 7a-hydroxylase, with approximately 56% identity over the coding region. At the polypeptide level the mouse ORF shows 81% identity to the rat Hct-1 polypeptide over 414 amino acids; the precise degree of similarity may be different as the full protein sequence of rat Hct-1 is not known. Both the human (CYP7) and rat cholesterol 7a-hydroxylase polypeptides share 39% amino acid sequence identity to mouse Hct-1. FIG. 4A presents the alignment of mouse Hct-1 polypeptide with human CYP7.

The N-terminus of the Hct-1 polypeptide is hydrophobic, a feature shared by microsomal CYP's. This portion of the polypeptide is thought to insert into the membrane of the endoplasmic reticulum, holding the main bulk of the protein on the cytoplasmic side. Consistent with microsomal CYP's, the N-terminus lacks basic amino acids prior to the hydrophobic core (amino acids 9–34).

Several alignment studies have previously highlighted conserved regions within CYP polypeptides. We therefore inspected the Hct-1 sequence for these conserved regions. CYP's contain a highly conserved motif, FxxGxxxCxG (xxxA) (SEQ ID NO:10), present in 202 of the 205 compiled sequences (Nelson et al., supra), that is thought to represent the heme binding site. The arrangement of amino acids around the cysteine residue has been postulated to preserve the three-dimensional structure of this region for ligand binding. This motif is fully conserved in Hct-1 (FIG. 4B). A second conserved domain is also present in CYP's responsible for steroid interconversions. While this domain is largely conserved in Hct-1 an invariant Pro residue is replaced, in Hct-1, by Val (FIG. 4C); the rat Hct-1 polypeptide also contains a Val residue at this position.

2.3 Expression pattern of mouse Hct-1

Figure 2C:
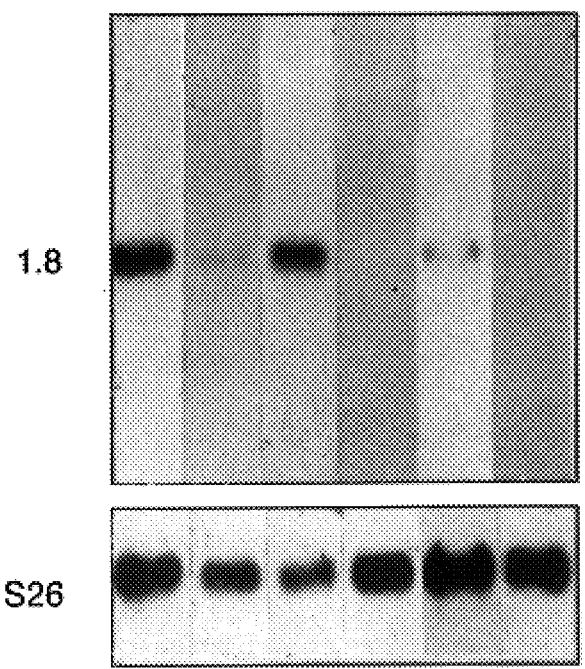

To verify enriched expression of Hct-1 in hippocampus we performed Northern and in situ hybridization analyses on mouse material. In contrast to the situation in rat, the 1.4 kb clone 12 detected only a 1.8 kb transcript; the 2.1 kb and 5.0 kb transcripts were absent from all tissues examined (FIG. 2C). The apparent absence of the 2.1 kb transcript may only reflect a lower abundance of this transcript because at least some mouse cDNA clones extend beyond the upstream polyadenylation site which is thought, in rat, to generate the shorter (1.8 kb) transcript.

Figure 5A:
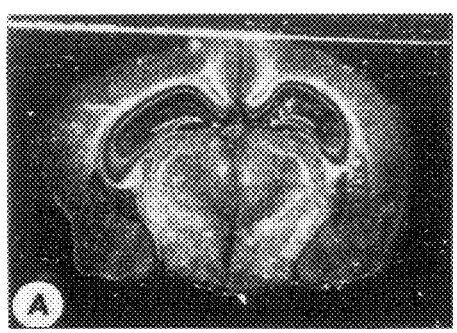
Figure 5B:
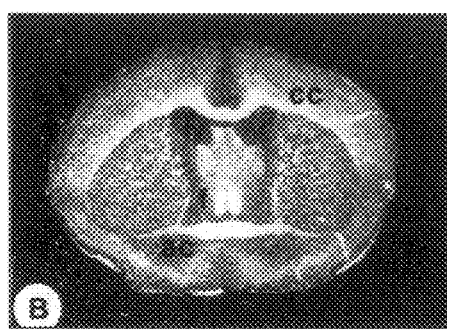
Figure 5C:
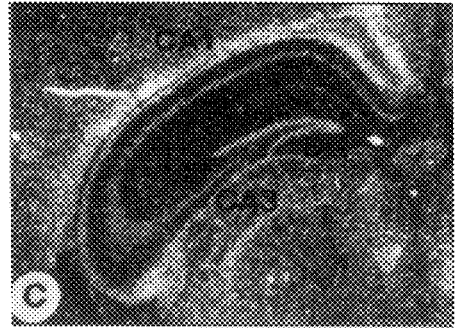
Figure 5D:

To refine this analysis, a 42-mer oligonucleotide was designed according to the DNA sequence of the 3' untranslated region of the cDNA clone upstream of the first polyadenylation site (materials and methods), so as to minimize cross-hybridization with other CYP mRNA's. Coronal sections of mouse brain were hybridized to the $^{35}$S-labelled probe and, after emulsion dipping, exposed for autoradiography (FIG. 5). Transcripts were detected throughout mouse brain, with no evidence of restricted expression in the hippocampus (FIGS. 5A,B). Strongest expression was observed in the corpus callosum, the anterior commisure and fornix while, as in rat, hippocampal expression was particularly prominent in the dentate gyrus (FIG. 5C). Moderate expression levels, comparable to those observed in hippocampus, were observed in cerebellum, cortex and olfactory bulb.

2.4 The structure of the mHct-1 gene.

The use of homologous recombination to manipulate the mouse Hct-1 gene requires knowledge of the intron-exon structure of the gene. Sequences upstream of the first Hct-1 exon could also be analysed for elements which contribute to the transcriptional regulation of Hct-1 expression. For these reasons, the organisation of the mouse Hct-1 gene was investigated.

Figure 7A:
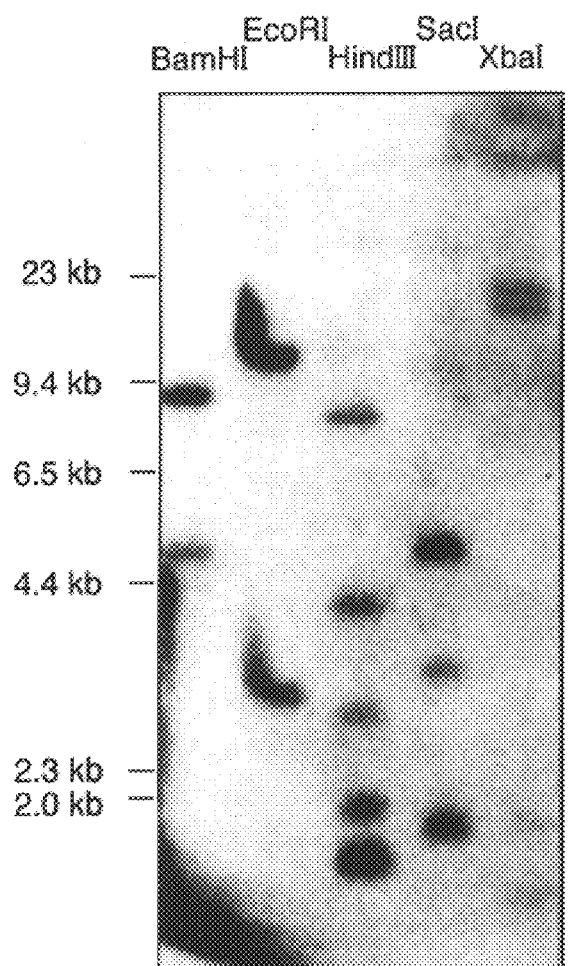
Figure 7B:
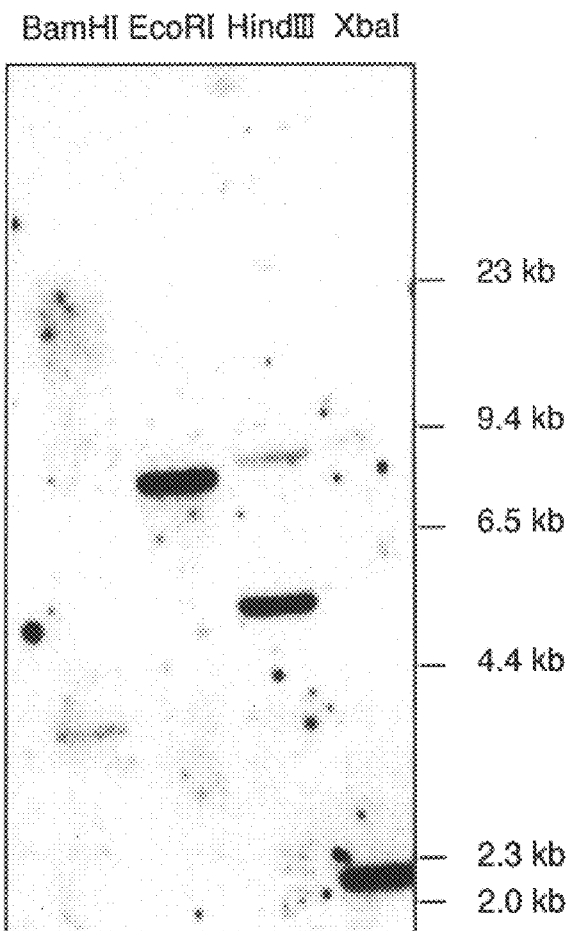

To assess the complexity of the Hct-1 gene in the genome, that is, whether the Hct-1 gene is present as a single copy in the haploid mouse genome, and to assist in mapping of mHct-1 phage clones, the 1.8 kb full length mouse Hct-1 clone was $^{32}$P-labelled by random primer labelling and used as a probe on a Southern blot of mouse genomic DNA (FIG. 7(a)). Under high stringency conditions the Hct-1 probe recognised a small number of bands within the mouse genomic digests, suggesting that Hct-1 is present in the mouse genome as a single copy gene. To confirm this, the original 0.3 kb cDNA clone, 14.5a, was used to probe a rat genomic Southern blot. The smaller probe hybridised to a single band in BamHI-, EcoRI-, and XbaI -digested genomic rat DNA (FIG. 7(b)).

A mouse genomic DNA library (a gift from A. Reaume, Toronto) prepared from ES cells derived from the 129 mouse strain was screened for genomic clones containing mHct-1 exonic sequence. 750,000 recombinant phage of the lambda DASH II library were plated at a density of 50,000 recombinants per 15 cm plate. Duplicate lifts were made and probed with the 1.4 kb rat Hct-1 clone. After the primary screen, 5 clones were isolated. After secondary screening, three of these phage clones were positive and were purified.

Small scale phage DNA was prepared from each phage lysate and cut with NotI to release the inserts. No internal NotI sites were found in any of the clones. Clone I-2 contained a 14 kb insert; clone I-6 contained a 15 kb insert, and clone I-11 contained a 12 kb insert.

Figure 8:
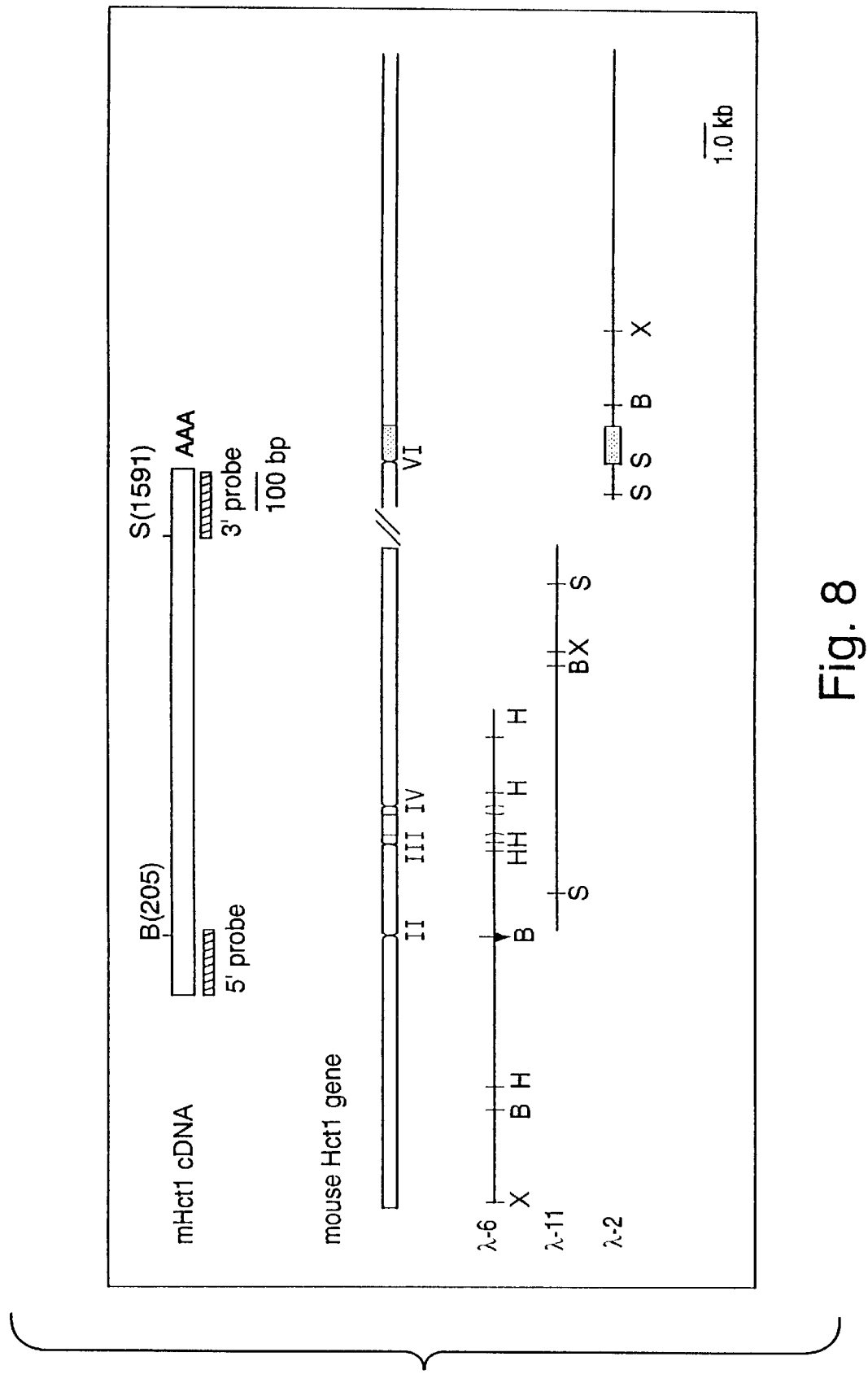

These phage clones were mapped by a combination of restriction enzymes which either cut the lambda clones rarely, or by using restriction sites found in the mHct-1 cDNA sequence (FIG. 3). A 5' probe was created using a 200 bp fragment from the 5' end of mHct-1 cDNA as a probe; this segment extended from the internal BamHI site to an EcoRI site located in the polylinker. The 200 bp 3' cDNA probe extended from the SacI site to the polylinker NotI site. Exon-intron boundaries were determined by subcloning of exon-containing genomic DNA fragments and sequencing (FIG. 8).

Phage clones I-6 and I-11 represented 20 kb of contiguous sequence of the Hct-1 locus. I-2 does not overlap withI-6 or I-11, thus the map of the Hct-1 gene in mouse is incomplete. However, the present map shows that mHct-1 spans at least 25 kb of the genome. At least two exons are contained within I-6. The first exon (referred to as exon II) contains 133 bp of coding sequence, followed by exon III, located 4.0 kb downstream. The 3' boundary of this latter exon is not defined, however approximately 400 bp downstream of its 3' boundary commences exon IV, which together comprise 797 bp of coding sequence. Exon III and IV are also represented in the overlapping sequence of I-11. A fourth exon of at least 345 bp was identified in I-2 (referred to as exon VI). The 3' boundary of this exon has not been identified, thus it is not known whether this contains the remaining coding sequence or if there are additional exons.

The following Table provides a summary of the exon-intron structure of Hct-1 (incomplete) and comparison to human CYP7 gene structure. * indicates that these exons are not cloned and are not necessarily one exon. ** indicates that the 3' boundary of exon VI is not confirmed and may not necessarily be the final exon.

| Exon | cDNA sequence represented | exon size (bp) | CYP7 exon (bp) |
|---|---|---|---|
| I* | 1–142 | 142 | 144 |
| II | 143–275 | 133 | 241 |
| III | 276–? | 797 | 587 |
| IV | ?–1072 | " | 131 |
| V* | 1073–1246 | 174 | 176 |
| VI** | 1247–(1821) | (575) | 1596 |

As shown in the Table, cDNA sequence from nucleotides 1073–1246 is not represented in the identified exons and must be represented in a separate exon. 142 bp of 5' sequence and 227 bp of 3' sequence have not yet been located in the genomic clones. The remaining 5' sequence is most likely contained in one exon, as the 5' probe (BamHI fragment) consistently recognised two bands by Southern analysis (one of which is exon II sequence). The remaining 3' sequence has not been located and may be part of exon VI or be encoded by a separate exon.

3. ISOLATION OF HUMAN GENOMIC SEQUENCES FOR HCT-1

3.1 Conservation of Hct-1 in humans.

The evolutionary conservation of a gene supports a functionally significant role for that gene in the organism. The conservation of Hct-1 in rodents has been demonstrated by the cloning of the rat and mouse cDNAs for Hct-1. To establish the presence of the Hct-1 gene in the human genome, Southern blotting of human DNA was performed. The rat 1.4 kb clone of Hct-1 was used as a radiolabelled probe and gave strong signals from all three species (FIG. 6). A number of hybridising fragments appear to be conserved between species, suggesting conservation of the Hct-1 gene structure. There is a conserved 1.4 kb HindIII band between mouse and rat, while human DNA contains a slightly larger HindIII band of 1.6 kb. Also an EcoRI fragment of 11 kb is conserved in human and rat Hct-1. Conservation of Hct-1 gene structure is also supported from the cDNA digestion patterns of mouse and rat (see FIGS. 6 and 7), where the SacI, HindIII and PstI sites are conserved between the rodent species.

3.2 A single gene for Hct-1 in mouse, rat and human

Because CYP's comprise a family of related enzymes we wished to determine whether close homologs of Hct-1 are present in the mammalian genome. The rat Hct-1 probe (1.4 kb) was used to probe a genomic Southern blot of rat, mouse and human DNA. In FIG. 6 the probe revealed a simple pattern of cross-hybridizing bands in all DNA's examined. In BamHI-cut human DNA only a single major cross-hybridizing band (4 kb) was detected (FIG. 6), while reprobing with the 300 nt. clone 14-5a yielded, in each lane, a single cross-hybridizing band (not shown). These data argue that a single conserved Hct-1 gene is present in mouse, rat and human, and that the mammalian genome does not contain very close homologs of Hct-1 that would be detected by cross-hybridization (>70–80% homology).

3.3 Isolation of sequences encoding human Hct-1

The rat cDNA clone 14.5a-1 2 was used to probe a Southern blot of human genomic DNA digested with BamHI according to standard procedures. A single band at 3.8 kb was identified that cross-hybridises with the probe. Accordingly, 20 μg of human genomic DNA was cleaved to completion with BamHI, resolved by agarose gel electrophoresis, and the size range 3.4–4.2 kb selected by reference to markers run on the same gel. The gel fragment was digested by agarase treatment, DNA was purified by phenol extraction and ethanol precipitation, and ligated into BamHI-cut bacteriophage lambda ZAP vector (Stratagene). Following packaging in vitro and plating on a lawn of *E. coli* strain XL1-Blue , plaque lifts of 100,000 clones were screened for hybridisation to the rat cDNA. 12 positive signals were identified and all contained a 3.8 kb insert. One was selected and the segment was partially sequenced, identifying two regions of high homology to the rat (and mouse) cDNA's and corresponding to exons 3 and 4. FIG. 9 presents the nucleotide sequence and FIG. 10 compares the human Hct-1 translation product with the cognate mouse polypeptide.

To extend this characterisation, the 3.8 kb BamHI fragment obtained from the size-selected library was used to screen a genomic library of human DNA prepared by partial Sau3A cleavage and insertion of 14–18 kb fragments into a bacteriophage lambda vector according to standard techniques (gift of Dr. P. Estibeiro, CGR). Positive clones were obtained, and restriction mapping of one confirmed that it contains approximately 14 kb of human DNA encompassing the exons identified above and further regions of the Hct-1 gene; together the different genomic clones are thought to encompass the entire Hct-1 gene. The human genomic sequence may be used to screen human cDNA libraries for full length cDNA clones; alternatively, following complete DNA sequence determination the human genomic sequence may be expressed in mammalian cells by adjoining it to a suitable promoter sequence and cDNA prepared from the correctly spliced mRNA product so produced. Finally, the genomic Hct-1 sequence would permit the entire coding sequence to be deduced so permitting the assembly of a full length Hct-1 coding sequence by de novo synthesis.

Figure 12A:
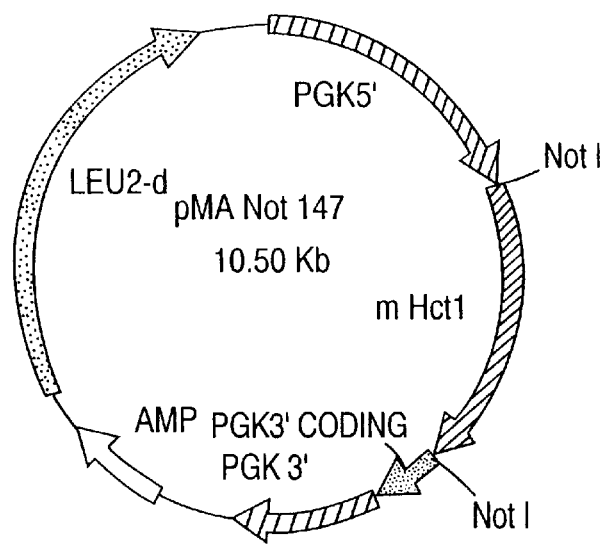
Figure 12B:
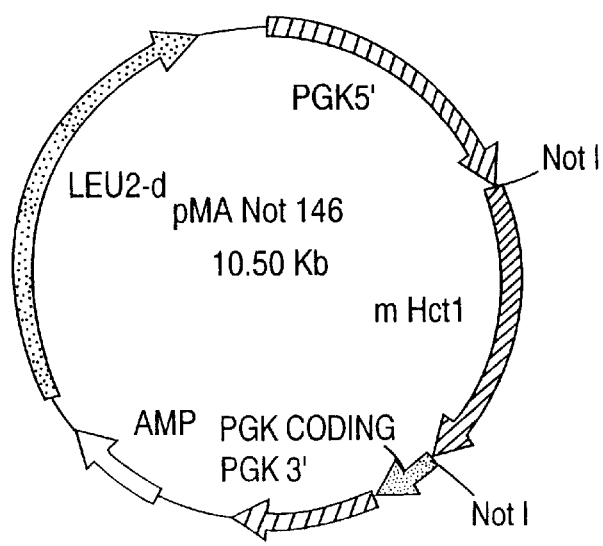

3.4 Expression of Hct-1 protein for enzymatic activity analysis 3.4.1. Expression of Hct-1 polypeptide in yeast cells Recombinant yeast strains are useful vehicles for the production of heterologous cytochrome P450 proteins. It would be possible to express any of the mammalian Hct-1's in yeast, but for simplicity we selected the mouse Hct-1 clone 35. To introduce the mouse Hct-1 (mHct-1) coding sequence into yeast the expression vector pMA91 (Kingsman et al., Meth. Enzymol. 185: 329–341, 1990) was employed. The unique BglII site in pMA91 was converted to a NotI site by inserting the oligonucleotide 5'GATCGCG-GCCGC3' (SEQ ID NO:11) according to standard procedures. Following cleavage of the resulting plasmid (pMA91-Not) with NotI the mHct-1 cDNA clone 35 was introduced, placing mHct-1 expression under the control of the yeast PGK (phosphoglycerokinase) promoter for high level expression in yeast cells (FIG. 12A). A similar construct utilising the mHct-1 cDNA clone 35 is depicted in FIG. 12B. Expression of mHct-1 in yeast using these plasmid permits the purification of the protein and determination of substrate specificity.

3.4.2. Expression of Hct-1 polypeptide in vaccinia virus

Expression in vaccinia virus is a routine procedure and has been widely employed for the expression of heterologous cytochromes P450 in mammalian cells, including HepG2 and Hela cells (Gonzalez, Aoyama and Gelboin, Meth. in Enzymol. 206: 85–92, 1991; Waxman et al., Archives Biochem. Biophys 290, 160–166,1991). Accordingly we selected plasmid pTG186-poly (Lathe et al., Nature 326, 878–880, 1987) as the transfer/expression vector, although other similar vectors are widely available and may also be employed.

To demonstrate the expression of mammalian Hct-1's in vaccinia virus, for simplicity we selected the mHct-1 clone 35. Similar techniques are applicable to rat and human Hct-1's. To enhance expression we elected to modify the 5' end to conform better to the translation consensus for mammalian cells (YYAYYATGR) though this modification may not be essential.

Accordingly, two oligonucleotides were designed corresponding to the 5' and 3' regions of the mouse cDNA.

The 5' oligonucleotide:

(5'-GGCCCTCGAGCCACCATGCAGGGGAGCCACG-3')

(SEQ ID NO:12) is homologous to the region surrounding the translation initiation site but converts the sequence immediately prior to the ATG to the sequence CCACC; in addition, the oligonucleotide contains a XhoI restriction site for subsequent cloning. The 3' oligonucleotide (GGCCGAATTCTCAGCTTCTCCAAGAA) was chosen according to the sequence downstream of the translation stop site and contains, in addition, an EcoRI site for subsequent cloning. These oligonucleotides were employed in polymerase chain reaction (PCR) amplification through 5 cycles on the clone 35 template; the products were applied to an agarose gel and the desired product band at 1.65 kb was cut out and extracted by standard procedures.

Figure 13:
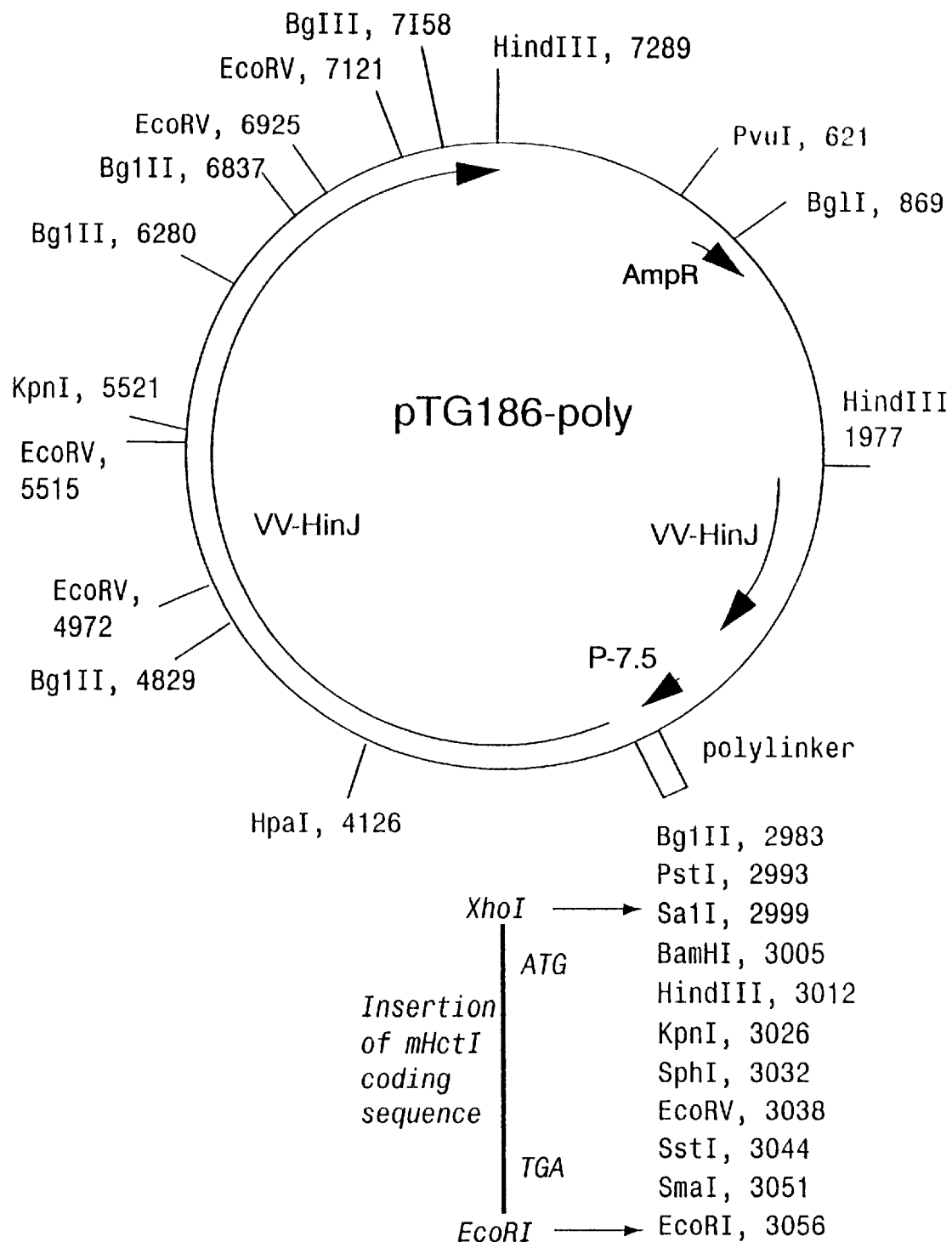

Following cleavage with XhoI and EcoRI the modified fragment was introduced between the EcoRI and SalI sites of pTG186-poly, generating pVV-mHct-1. Recombinational exchange was used to transfer the expression vector to the vaccinia virus genome according to standard procedures, generating VV-mHct-1, as depicted in FIG. 13. This recombinant will permit the expression of high levels of mHct-1 and the identification of the substrate specificity of the protein, as well as the production of antibodies directed against mHct-1.

To identify the product of P450-mediated metabolism, microsomes may easily be prepared (Waxman, Biochem. J. 260: 81–85, 1989) from vaccinia-infected cells: these are incubated with labelled precursors, eg. steroids, and the product identified by thin layer chromatography according to standard procedures (Waxman, Methods in Enzymology 206:462–476).

The Hct-1 provided according to this invention thereby provides a route for the large-scale production of the product described above, for instance a modified steroid, by expressing the P450 in a recombinant organism and supplying the substrate for conversion. It will also be possible to engineer recombinant yeast, for instance, to synthesise the substrate for the Hct-1 P450 in vivo, so as to allow production of the Hct-1 product from yeast supplied with a precursor, for instance cholesterol or other molecule, if that yeast is engineered to contain other P450's or modifying enzymes. It may be possible for Hct-1 to act on endogenous sterols and steroids in yeast to yield product.

Finally, the Hct-1 product may be part of a metabolic chain, and recombinant organisms may be engineered to contain P450's or other enzymes that convert the Hct-1 product to a subsequent product that may in turn be harvested from the organism.

4. DISCUSSION

In experiments to characterize transcripts enriched in the hippocampal formation we isolated cDNA clones corresponding to Hct-1 (hippocampal transcript) from a library prepared from rat hippocampus RNA. In rat, expression appeared to be most abundant in hippocampus with some expression in cortex and substantially less expression other in brain regions. Elsewhere in the body transcripts were only detected in liver and, to a lesser extent, in kidney; expression was barely detectable in ovary, testis and adrenal, also sites of steroid transformations. Hepatic expression was sexually dimorphic with Hct-1 mRNA barely detectable in female liver. In rat brain and liver, Hct-1 identifies two transcripts of 1.8 and 2.1 kb that appear to be generated by alternative polyadenylation; a 5.0 kb transcript weakly detected in brain is thought not to originate from the Hct-1 gene but instead encodes a polypeptide related to the GTPase activating protein, ABR (active BCR-related).

Sequence analysis of Hct-1 cDNA clones revealed an extensive open reading frame encoding a protein with homology to cytochromes P450 (CYP's), a family of heme-containing mono-oxygenases responsible for a variety of steroid and fatty acid interconversions and the oxidative metabolism of xenobiotics. Although the mouse cDNA coding region appears complete, the absence of a consensus translation initiation site flanking the presumed initiation codon could indicate that Hct-1 polypeptide synthesis is subject to regulation at the level of translation initiation.

Homology was highest with rat and human cholesterol 7α-hydroxylase, known as CYP7. While related, Hct-1 is clearly distinct from CYP7, sharing only 39% homology over the full length of the protein. CYP polypeptides sharing greater than 40% sequence identity are generally regarded as belonging to the to the same family, and Hct-1 and CYP7 (39% similarity) are hence borderline. The conservation of other unique features between Hct-1 and CYP7 however argues for a close relationship and Hct-1 has been provisionally named 'CYP7B' by the P450 Nomenclature Committee (D. R. Nelson, personal communication).

From the Hct-1 leader sequence we surmise that the Hct-1 polypeptide resides, like CYP7, in the endoplasmic reticulum and not in mitochondria, the other principal cellular site of CYP activity. The strictly conserved heme binding site motif FxxGxxxCxG(xxxA) (SEQ ID NO:10) is clearly present in Hct-1 (residues 440–453). It is of note that the 'steroidogenic domain', conserved in many CYP's responsible for steroid interconversions, is also present in Hct-1 (amino acids 348–362), except that a consensus Pro residue is replaced by Val in both the mouse and rat Hct-1 polypeptides. Of previously known 34 CYP sequences, only 4 contain an amino acid residue other than Pro at this position. Whereas 2 of these harbour an unrelated amino acid (Glu; CYP3A1, CYP3A3), interestingly, a Val residue is present in bovine CYP17 (steroid 17α-hydroxylase, 44) at a position equivalent to that in Hct-1 while human CYP17 harbours a conservative substitution at this site (Leu;44). Despite this similarity, however, the overall extent of homology between Hct-1 and CYP17 (22.5%, not shown) is lower than with CYP7 (39%).

Neither Hct-1 and CYP7 appear to contain a conserved $O_2$ binding pocket (equivalent to residues 285–301 in Hct-1). Crystallographic studies on the bacterial CYP101 indicated that a Thr residue (corresponding to position 294 in Hct-1) disrupts helix formation in that region and is important in providing a structural pocket for an oxygen molecule. Site-directed mutagenesis of this Thr residue in both CYP4A1 and CYP2C11 demonstrated that this region can influence substrate specificity and affinity. In both Hct-1 and CYP7 the conserved Thr residue is replaced by Asn. This modification suggests that Hct-1 and CYP7 are both structurally distinct from other CYP's in this region; this may be reflected both in modified oxygen interaction and substrate choice.

The sexual dimorphism of Hct-1 expression observed in rat resembles that observed with a number of other CYP's. CYP2C12 is expressed preferentially in liver of the female rat while, like Hct-1, CYP2C11 is highly expressed in male liver but only at low levels in the female tissue. This dimorphic expression pattern of CYP2C family members is thought to be determined by the dimorphism of pulsatility of growth hormone secretion. Brain expression of Hct-1 is not subject to this control suggesting that regulatory elements determining Hct-1 expression in brain differ from those utilized in liver. However, we have not examined species other than rat; it cannot be assumed that the same regulation will exist in other species. Indeed, sexually dimorphic gene expression is not necessarily conserved between different strains of mouse.

Expression of Hct-1 was widespread in mouse brain. The expression pattern was most consistent with glial expression but further experiments will be required to compare neuronal and non-neuronal levels of expression. In mouse brain only the 1.8 kb transcript was detected, though cDNA's were obtained corresponding to transcripts extending beyond the first polyadenylation site; such extended transcripts are thought to give rise to the 2.1 kb transcript in rat. This suggests the downstream polyadenylation site seen in rat Hct-1 is under-utilized in mouse Hct-1 or absent. While in situ hybridization studies of Hct-1 in rat brain were inconclusive, a difference in expression pattern between mouse and rat appears likely; further work will be required to confirm this. However, such a difference would be unsurprising because cytochromes P450 are well known to vary widely in their level and pattern of expression in different species; for instance, hepatic testosterone 16-hydroxylation levels differ by more than 100-fold between guinea pig and rat.

Our data indicate that the Hct-1 gene is present in rat, mouse and human, and there appear to be no very close relatives in the mammalian genome. While CYP genes are scattered over the mouse and human genomes, CYP subfamilies can cluster on the same chromosome. For instance, the human CYP2A and 2B subfamily genes are linked to chromosome 19, CYP2C and 2E subfamilies are located on human chromosome 10, and the mouse cyp2a, 2b and 2e subfamilies are present on mouse chromosome 7. The gene encoding human cholesterol 7α-hydroxylase (CYP7) is located on chromosome 8q11-q12.

Together our data argue that Hct-1 and CYP7 are closely related: this suggests that the substrate for Hct-1, so far unknown, is likely to be related to cholesterol or one of its steroid metabolites. This interpretation is borne out by the presence, in Hct-1, of the steriodogenic domain conserved in a number of steroid-metabolizing CYP's. While experiments are underway to determine the substrate specificity of Hct-1, the possibility that Hct-1 acts on cholesterol or its steroid metabolites in brain is of some interest. CYP7 (cholesterol 7α-hydroxylase) is responsible for the first step in the metabolic degradation of cholesterol. This is of note in view of the association of particular alleles of the APOE gene encoding the cholesterol transporter protein apolipoprotein E with the onset of Alzheimer's disease, a neurodegenerative condition whose cognitive impairments are associated with early dysfunction of the hippocampus.

What role might Hct-1 play in the brain? In the adult CYP's are generally expressed abundantly in liver, adrenal and gonads, while the level of CYP activity in brain is estimated to be 0.3 to 3% of that found in liver (see 58). Because levels of Hct-1 mRNA expression in rat and mouse brain far exceed those in liver it could be argued that the primary function of Hct-1 lies in the central nervous system. The documented ability of cholesterol-derived steroids to interact with neurotransmitter receptors and modulate both synaptic plasticity and cognitive function suggests that Hct-1 and its metabolic product(s) may regulate neuronal function in vivo.

5. SUMMARY

Hct-1 (hippocampal transcript) was detected in a differential screen of a rat hippocampal cDNA library. Expression of Hct-1 was enriched in the formation but was also detected in rat liver and kidney, though at much lower levels; expression was barely detectable in testis, ovary and adrenal. In liver, unlike brain, expression was sexually dimorphic: hepatic expression was greatly reduced in female rats. In mouse, brain expression in was widespread, with the highest levels being detected in corpus callosum; only low levels were detected in liver. Sequence analysis of rat and mouse Hct-1 cDNAs revealed extensive homologies with cytochrome P450's (CYP's), a diverse family of heme-binding monooxygenases that metabolize a range of substrates including steroids, fatty acids and xenobiotics. Among the CYP's, Hct-1 is most similar (39% at the amino acid sequence) to cholesterol 7α-hydroxylase (CYP7), and contains the diagnostic steriodogenic domain present in other steriod-metabolizing CYPs, but clearly represents a type of CYP not previously reported. Genomic Southern analysis indicates that a single gene corresponding to Hct-1 is present in mouse, rat and human. Hct-1 is unusual in that, unlike all other CYP's described, the primary site of expression is in the brain. Similarity to CYP7 and other steroid-metabolizing CYP's argues that Hct-1 plays a role in steroid metabolism in brain, notable because of the documented ability of brain-derived steroids (neurosteroids) to modulate cognitive function in vivo.

6. DETAILS OF EXPERIMENTAL PROTOCOLS

Northern analysis—Total RNA was extracted by tissue homogenization in guanidinium thiocyanate according to a standard procedure and further purified by centrifugation through a CsCl cushion. Where appropriate, polyA-plus RNA was selected on oligo-dt cellulose. Electrophoresis of RNA (10 μg) on 1% agarose in the presence of 7% formaldehyde was followed by capillary transfer to nylon membranes, baking (2 h, 80° C.), and rinsing in hybridization buffer (0.25 M NaPhosphate, pH 7.2; 1 mM EDTA, 7% sodium dodecyl sulphate [SDS], 1% bovine serum albumin) as described (Church et al., supra). Probes were prepared by random-priming of DNA polymerase copying of denatured double-stranded DNA. Hybridization (16 h, 68° C.) was followed by washing (3 times, 20 mM NaPhosphate pH 7.2, 1 mM EDTA, 1% SDS, 20 min.) and membranes exposed for autoradiography. The loading control probe was a 0.5 kb cDNA encoding the ubiquitously expressed rat ribosomal protein S26.

In situ hybridization--Synthetic Hct-1 oligonucleotide probes 5'-dGACAGGTTTTGTGACCCAAAACAAACTGGATGG ATCGCAATC-3'(SEQ ID NO:14)(rat, 55% G+C) and 5'-ATCACGGAGCTCAGCACATGCAGCCTTACTCTGC AAAGCTTC-3'(SEQ ID NO:15)(mouse—48% G+C) were labelled using terminal transferase (Boehringer Mannheim) and α-$^{35}$S-dATP (Amersham) according to the manufacturer's instructions.

The control probe, 5'-dAGCCTTCTGGGTCGTAGCTGACTCCTGCTGCTG AGCTGCAACAGCTTT-3'(SEQ ID NO:16)(56% G+C) was based on human opsin cDNA. Frozen coronal 10 μm sections of brain were fixed (4% paraformaldehyde, 10 min), rinsed, treated with proteinase K (20 μg/ml in 50 mM Tris.HCl, pH 7.4, 5 mM EDTA, 5 min), rinsed, and refixed with paraformaldehyde as before. Following acetylation (0.25% acetic anhydride, 10 min) and rinsing, sections were dehydrated by passing though increasing ethanol concentrations (30, 50, 70, 85, 95, 100, 100%, each for 1 minute except the 70% step [5 min]). Following CHCl$_3$ treatment (5 min), and rinsing in ethanol, sections were dried before hybridization. Hybridization in buffer (4×standard saline citrate [1×SSC=0.15 M NaCl, 0.015 M Na$_3$citrate], 50% v/v formamide, 10% w/v dextran sulphate, 1x Denhardt's solution, 0.1% SDS, 500 μg/ml denatured salmon sperm DNA, 250 μg/ml yeast tRNA) was for 16 h at 37° C. Slides were washed (4×15 min., 1×SSC, 60° C.; 2 x 30 min., 1×SSC, 20° C.), dipped into photographic liquid emulsion (LM-1, Amersham), exposed and developed according to the manufacturer's specifications. Slides were counterstained with 1% methyl green.

Southern hybridization—Genomic DNA prepared from mouse or rat liver, or from human lymphocytes, was digested with the appropriate restriction endonuclease, resolved by agarose gel electrophoresis (0.7%) and transferred to Hybond-N membranes. Following baking (2 h, 80° C.), hybridization conditions were as described for Northern analysis.

Hybridisation Conditions. Hybridisation conditions used were based on those described by Church and Gilbert, Proc. Natl. Acad. Sci. USA (1984) 81, 1991–1995.

1. Filters were pre-wet in 2XSSC.
2. The hybridisation was performed in a rotating glass cylinder (Techne Hybridiser ovens). 10 ml of Hybridisation Buffer was added to the cylinder with the filter.
3. Prehybridisation and hybridisation were carried out at 68° C. unless otherwise specified.
4. The filters were prehybridised for 30 minutes, after which the probe was added directly and hybridisation proceeded overnight. (Double-stranded probes were denatured by boiling for 2 minutes, then placing on ice).

5. Washes were performed at 68° C. (unless otherwise stated) with 2 changes of Wash Buffer I for 10 minutes each, followed by three changes of Wash Buffer II each for 20 minutes.
6. The filters were blotted dry, but not allowed to dry out, then placed between Saran wrap, and against X-ray film for autoradiography.

Hybridisation Buffer:
   0.25 M sodium phosphate pH 7.2
   1 mM EDTA
   7% SDS
   1% BSA Wash Buffer I:
   20 mM sodium phosphate pH 7.2
   2.5% SDS
   0.25% BSA
   1 mM EDTA Wash Buffer II:
   20 mM sodium phosphate pH 7.2
   1 mM EDTA
   1% SDS Screening of Bacteriophage lambda libraries. The rat hippocampus cDNA library was oligo-(dT)-NotI primed and cloned in lambda ZAP II (Stratagene) with an EcoRI adaptor at the 5' end, and was prepared in the lab by Miss M. Richardson and Dr. J. Mason; the mouse liver cDNA library was oligo-(dT)-primed and cloned into lambda gt10 with EcoRI/NotI adaptors, and was a gift from Dr. B. Luckow, Heidelberg; the mouse ES cell genomic library was cloned from a partial Sau3A digest into lambda DASH II (Stratagene), and was a gift from A. Reaume, Toronto.

The libraries were screened as described above by hybridization.

In vivo excision of pBluescript from lambda ZAP II vector was performed using the ExAssist/SOLR system (Stratagene, 200253).

In situ hybridisation. Frozen 10 μ coronal sections of rat and mouse brains were provided by Dr. M. Steel.

Hybridisation Conditions All probes were oligonucleotides which were labelled by homopolymer tailing using a-$^{35}$S-dATP and terminal transferase.

The sequences or references of the oligonucleotides used as probes for in situ hybridisation were as follows (SEQ ID NOS: 14, 15, & 17, respectively):

rat Hct-1 (a 45-mer, beginning 26 nt 5' from the polyA tail, nucleotides 1361–1403 in FIG. 4.2) (for relative position in mouse gene, see FIG. 4.3)

5'-GACAGGTTTTGTGACCCAAAACAAACTG-
   GATGGATCGCAATC-3'

Nathans mouse Hct-1 (nt 1558–1599)

5'-ATCACGGAGCTCAGCACATGCAGCCT-
   TACTCTGCAAAGCTTC-3' rat clone 13 (a 42-mer, beginning 112 nt 5' from polyA tail)

5'-TATATCCATACCAACTTATTGGGAGTC-
   CCATCCTACCTCATCAGC-3' rat/mouse muscarinic receptor M1 (Buckley et al., 1988)
rat/mouse opsins (Nathans et al., Science (1986) 232, 193–202)

1. The prepared $^{35}$S -tailed probe (resuspended in 10 mM DTT in TE) was diluted to 2×10$^6$cpm/ml in hybridisation buffer. DTT is also added to this mixture to a final concentration of 50 mM.
2. 100 ml of the probe mixture was carefully layered onto each microscope slide. A piece of parafilm cut to the size of the microscope slide was then layered over the probe mixture, allowing the probe and hybridisation mixture to cover all the sections. Air bubbles under the parafilm were avoided.
3. The slides were placed in a humidified container, sealed, and incubated at 37° C. overnight.
4. After hybridisation, the parafilm was carefully removed using forceps.
5. The slides were placed back in Coplin jars, and the hybridised sections washed in four changes of 1XSSC for 15 minutes at 55° C. or 60° C., and then two changes of 1XSSC for 30 minutes at room temperature.
6. The slides were rinsed briefly in dH$_2$O, then left to air dry.

Hybridisation Buffer*
   4XSSC
   50% (v/v) deionised formamide
   10% (w/v) dextran sulphate
   1X Denhardt's solution
   0.1% (w/v) SDS
   500 μg/ml ssDNA
   250 μg/ml yeast tRNA
   *buffer was de-gassed before use

7. FIGURE LEGENDS

FIG. 1. Sequence of partial rat Hct-1 cDNA and the encoded polypeptide

The nucleotide sequence and translation product of the 1.4 kb cDNA clone 12 including additional clone 7 sequence (lower case). The two putative polyadenylation signals are underlined.

FIG. 2. Northern analysis of Hct-1 expression in adult rat and mouse brain

Panel A. Expression in rat brain and other tissues; panel B. sexually dimorphic expression in rat liver; panel C. Expression in mouse tissues. Poly-A$^+$ (A) or total (B,C) RNA from organs of adult animals were resolved by gel electrophoresis; the hybridization probe was rat Hct-1 cDNA clone 12 (1.4 kb), the probe for the loading control (below) corresponds to ribosomal protein S26. Tissues analysed are: Hi, hippocampus; RB, remainder of brain lacking hippocampus; Cx, cortex; Cb, cerebellum; Ob; olfactory bulb; Li, liver; He, heart; Th, thymus; Ki, kidney; Ov, ovary; Te, testis; Lu, lung.

FIG. 3. Mouse Hct-1 cDNA and the sequence of the encoded polypeptide

The restriction map of the cDNA (above) corresponds to the compilation of two independent clones sequenced; the cross-hatched box indicates the coding region. The nucleotide sequence and translation product (below) derives from this compilation. Lower case sequences indicate the 59 additional 5' nucleotides in clone 40 and the 99 additional 3' nucleotides in clone 35. The putative polyadenylation site is underlined.

FIG. 4. Alignment of mouse Hct-1 with human CYP7 (cholesterol 70-hydroxylase, Noshiro and Okuda, 1990) and other steroidogenic P450s Panel A: ID entical amino acids are indicated by a bar; hyphens in the amino acid sequences indicate gaps introduced during alignment. The N-terminal hydrophobic leader sequences are underlined. The position of the conserved Thr residue within the O$_2$-binding pocket of other CYP's (43), but replaced by Asn in Hct-1 (position 294) and CYP7, is indicated by an asterisk. Panels B,C: conserved residues in the heme-binding (residues 440–453, B) and steroidogenic (residues 348–362, C) domains conserved between Hct-1 and other similar CYP's (overlined in A). Sequences are human CYP7 (7a-hydroxylase; 37); bovine CYP17 (17α-hydroxylase; 44); human CYP11B1 (steroid β-hydroxylase; 45); human CYP21 B (21-hydroxylase; 11); human CYP11A1 (P450scc; cholesterol side-chain cleavage; 46); human CYP27 (27-hydroxylase; 47).

FIG. 5. Analysis of Hct-1 expression in adult mouse brain

The hybridization probe was a synthetic oligonucleotide corresponding to the 3' untranslated region of mouse Hct-1 cDNA. Panel a: coronal section; panel b: coronal section, rostral to a, showing hybridization in corpus callosum, cc; fornix, f; and anterior commissure, ac; panel c: enlargement of section through the hippocampus; DG, dentate gyrus; panel d: section adjacent to the section in a hybridized with an oligonucleotide specific for opsin (negative control).

FIG. 6. Southern analysis of Hct-1 coding sequences in mouse, rat and human

Total DNA was cleaved as indicated with restriction endonucleases B, BamHI; E, EcoRI; H, HindIII; X, XbaI; resolved by agarose gel electrophoresis, and probed with rat Hct-1 cDNA clone 12 before exposure to autoradiography.

FIG. 7 Genomic DNA Southern blot analysis of Hct-1

(a) Mouse genomic DNA probed with the full-length mouse Hct-1 cDNA clone. (b) Rat genomic DNA probed with clone 14.5a (original 0.3 kb clone of rHct-1). 10 μg of genomic DNA was digested with the indicated enzymes.

FIG. 8 Genomic map of mouse Hct-1 (incomplete)

Exons II, III, IV and VI are represented on the phage clones (filled boxes). Exons I and V are not located. As indicated in Table 4.1, the boundaries of exons II, III B (BamHI); H(HindIII); S(SacI); X(XhoI)

```
SEQ ID NOS 1-2

A   L   E   Y   Q   Y   V   M   K   N   P   K   Q   L   S   F   E   K   F   S
GCCTTGGAGTACCAGTATGTAATGAAAAACCCAAAACAATTAAGCTTTGAGAAGTTCAGC      60

R   R   L   S   A   K   A   F   S   V   K   K   L   L   T   N   D   D   L   S
CGAAGATTATCAGCGAAAGCCTTCTCTGTCAAGAAGCTGCTAACTAATGACGACCTTAGC     120

N   D   I   H   R   G   Y   L   L   L   Q   G   K   S   L   D   G   L   L   E
AATGACATTCACAGAGGCTATCTTCTTTTACAAGGCAAATCTCTGGATGGTCTTCTGGAA     180

T   M   I   Q   E   V   K   E   I   F   E   S   R   L   L   K   L   T   D   W
ACCATGATCCAAGAAGTAAAAGAAATATTTGAGTCCAGACTGCTAAAACTCACAGATTGG     240

N   T   A   R   V   F   D   F   C   S   S   L   V   F   E   I   T   F   T   T
AATACAGCAAGAGTATTTGATTTCTGTAGTTCACTGGTATTTGAAATCACATTTACAACT     300

I   Y   G   K   I   L   A   A   N   K   K   Q   I   I   S   E   L   R   D   D
ATATATGGAAAAATTCTTGCTGCTAACAAAAAACAAATTATCAGTGAGCTGAGGGATGAT     360

F   L   K   F   D   D   H   F   P   Y   L   V   S   D   I   P   I   Q   L   L
TTTTTAAAATTTGATGACCATTTCCCATACTTAGTATCTGACATACCTATTCAGCTTCTA     420

R   N   A   E   F   M   Q   K   K   I   I   K   C   L   T   P   E   K   V   A
AGAAATGCAGAATTTATGCAGAAGAAAATTATAAAATGTCTCACACCAGAAAAAGTAGCT     480

Q   M   Q   R   R   S   E   I   V   Q   E   R   Q   E   M   L   K   K   Y   Y
CAGATGCAAAGACGGTCAGAAATTGTTCAGGAGAGGCAGGAGATGCTGAAAAAATACTAC     560

G   H   E   E   F   E   I   G   A   H   H   L   G   L   L   W   A   S   L   A
GGGCATGAAGAGTTTGAAATAGGAGCACATCATCTTGGCTTGCTCTGGGCCTCTCTAGCA     600

N   T   I   P   A   M   F   W   A   M   Y   Y   L   L   Q   H   P   E   A   M
AACACCATTCCAGCTATGTTCTGGGCAATGTATTATCTTCTTCAGCATCCAGAAGCTATG     660

E   V   L   R   D   E   I   D   S   F   L   Q   S   T   G   Q   K   K   G   P
GAAGTCCTGCGTGACGAAATTGACAGCTTCCTGCAGTCAACAGGTCAAAAGAAAGGACCT     720

G   I   S   V   H   F   T   R   E   Q   L   D   S   L   V   C   L   E   S   A
GGAATTTCTGTCCACTTCACCAGAGAACAATTGGACAGCTTGGTCTGCCTGGAAAGCGCT     780

I   L   E   V   L   R   L   C   S   Y   S   S   I   I   R   E   V   Q   E   D
ATTCTTGAGGTTCTGAGGTTGTGCTCCTACTCCAGCATCATCCGTGAAGTGCAAGAGGAT     840
```

```
       M   D   F   S   S   E   S   R   S   Y   R   L   R   K   G   D   F   V   A   V
      ATGGATTTCAGCTCAGAGAGTAGGAGCTACCGTCTGCGGAAAGGAGACTTTGTAGCTGTC          900

F   P   P   M   I   H   N   D   P   E   V   F   D   A   P   K   D   F   R   F
      TTTCCTCCAATGATACACAATGACCCAGAAGTCTTCGATGCTCCAAAGGACTTTAGGTTT          960

D   R   F   V   E   D   G   K   K   K   T   T   F   F   K   G   G   K   K   L
      GATCGCTTCGTAGAAGATGGTAAGAAGAAAACAACGTTTTTCAAAGGAGGAAAAAAGCTG         1020

K   S   Y   I   I   P   F   G   L   G   T   S   K   C   P   G   R   Y   F   A
      AAGAGTTACATTATACCATTTGGACTTGGAACAAGCAAATGTCCAGGCAGATACTTTGCA         1080

I   N   E   M   K   L   L   V   I   I   L   L   T   Y   F   D   L   E   V   I
      ATTAATGAAATGAAGCTACTAGTGATTATACTTTTAACTTATTTTGATTTAGAAGTCATT         1140

D   T   K   P   I   G   L   N   H   S   R   M   F   L   G   I   Q   H   P   D
      GACACTAAGCCTATAGGACTAAACCACAGTCGCATGTTTCTGGGCATTCAGCATCCAGAC         1200

S   D   I   S   F   R   Y   K   A   K   S   W   R   S   ***
      TCTGACATCTCATTTAGGTACAAGGCAAAATCTTGGAGATCCTGAAAGGGTGGCAGAGAA         1260

GCTTAGCGGAATAAGGCTGCACATGCTGAGCTCTGTGATTTGCTGTACTCCCCAAATGCA         1320

GCCACTATTCTTGTTTGTTAGAAAATGGCAAATTTTTATTTGATTGCGATCCATCCAGTT         1380

TGTTTTGGGTCACAAAACCTGTCATAAAATAAAGCGCTGTCATGGTGTAaaaaaatgtca         1440 tggcaatcatttcaggataaggtaaaataacgttttcaagtttgtacttactatgatttt         1500 tatcatttgtagtgaatgtgcttttccagtaataaatttgcgccagggtgatttttttta         1560 attactgaaatcctctaatatcggttttatgtgctgccagaaaagtgtgccatcaatgga         1620 cagtataacaatttccagttttccagagaagggagaaattaagccccatgagttacgctg         1680 tataaaattgttctcttcaactataatatcaataatgtctatatcaccaggttacctttg         1740 cattaaatcgagttttgcaaaag                                              1763

SEQ ID NOS 3—4
      ggcaggcacagcctctggtctaagaagagagggcactgtgcagaagccatcgctccctaC          60

M   Q   G   A   T   T   L   D   A   A   S   P   G   P           14
      AGAGCCGCCAGCTCGTCGGGATGCAGGGAGCCACGACCCTAGATGCCGCCTCGCCAGGGC         120

L   A   L   L   G   L   L   F   A   A   T   L   L   L   S   A   L   F   L   L  34
      CTCTCGCCCTCCTAGGCCTTCTCTTTGCCGCCACCTTACTGCTCTCGGCCCTGTTCCTCC         180

T   R   R   T   R   R   P   R   E   P   P   L   I   K   G   W   L   P   Y   L  54
      TCACCCGGCGCACCAGGCGCCCTCGTGAACCACCCTTGATAAAAGGTTGGCTTCCTTATC         240

G   M   A   L   K   F   F   K   D   P   L   T   F   L   K   T   L   Q   R   Q  74
      TTGGCATGGCCCTGAAATTCTTTAAGGATCCGTTAACTTTCTTGAAAACTCTTCAAAGGC         300

H   G   D   T   F   T   V   F   L   V   G   K   Y   I   T   F   V   L   N   P  94
      ACATGGTGACACTTTCACTGTCTTCCTTGTGGGGAAGTATATAACATTTGTTCTGAACC         360

F   Q   Y   Q   V   T   K   N   P   K   Q   L   S   F   Q   K   F   S   S      114
      CTTTCCAGTACCAGTATGTAACGAAAAACCCAAAACAATTAAGCTTTCAGAAGTTCAGCA         420

R   L   S   A   K   A   F   S   V   K   K   L   T   D   D   D   L   N   E      134
      GCCGATTATCAGCGAAAGCCTTCTCTGTAAAGAAGCTGCTTACTGATGACGACCTTAATG         480

D   V   H   R   A   Y   L   L   L   Q   G   K   P   L   D   A   L   L   E   T  154
```

```
AAGACGTTCACAGAGCCTATCTACTTCTACAAGGCAAACCTTTGGATGCTCTTCTGGAAA      540

M   I   Q   E   V   K   E   L   F   E   S   Q   L   L   K   I   T   D   W   N     174

CTATGATCCAAGAAGTAAAAGAATTATTTGAGTCCCAACTGCTAAAAATCACAGATTGGA      600

T   E   R   I   F   A   F   C   G   S   L   V   F   E   I   T   F   A   T   L     194

ACACAGAAAGAATATTTGCATTCTGTGGCTCACTGGTATTTGAGATCACATTTGCGACTC      660

Y   G   K   I   L   A   G   N   K   K   Q   I   I   S   E   L   R   D   D   F     214

TATATGGAAAAATTCTTGCTGGTAACAAGAAACAAATTATCAGTGAGCTAAGGGATGATT      720

F   K   F   D   D   M   F   P   Y   L   V   S   D   I   P   I   Q   L   L   R     234

TTTTTAAATTTGATGACATGTTCCCATACTTAGTATCTGACATACCTATTCAGCTTCTAA      780

N   E   E   S   M   Q   K   K   I   I   K   C   L   T   S   E   K   V   A   Q     254

GAAATGAAGAATCTATGCAGAAGAAAATTATAAAATGCCTCACATCAGAAAAAGTAGCTC      840

M   Q   G   Q   S   K   I   V   Q   E   S   Q   D   L   L   K   R   Y   Y   R     274

AGATGCAAGGACAGTCAAAAATTGTTCAGGAAAGCCAAGATCTGCTGAAAAGATACTATA      900

H   D   D   P   E   I   G   A   H   H   L   G   F   L   W   A   S   L   A   N     294

GGCATGACGATTCTGAAATAGGAGCACATCATCTTGGCTTTCTCTGGGCCTCTCTAGCAA      960

T   I   P   A   M   F   W   A   M   Y   Y   I   L   R   H   P   E   A   M   E     314

ACACCATTCCAGCTATGTTCTGGGCAATGTATTATATTCTTCGGCATCCTGAAGCTATGG     1020

A   L   R   D   E   I   D   S   F   L   Q   S   T   G   Q   K   K   G   P   G     334

AAGCCCTGCGTGACGAAATTGACAGTTTCCTGCAGTCAACAGGTCAAAAGAAAGGGCCTG     1080

I   S   V   H   F   T   R   E   Q   L   D   S   L   V   C   L   E   S   T   I     354

GAATTTCAGTCCACTTCACCAGAGAACAATTGGACAGCTTGGTCTGCCTGGAAAGCACTA     1140

L   E   V   L   R   L   C   S   Y   S   S   I   I   R   E   V   Q   E   D   M     374

TTCTTGAGGTTCTGAGGCTGTGCTCATACTCCAGCATCATCCGAGAAGTGCAGGAGGATA     1200

N   L   S   L   E   S   K   S   F   S   L   R   K   G   D   F   V   A   L   F     394

TGAATCTCAGCTTAGAGAGTAAGAGTTTCTCTCTGCGGAAAGGAGATTTTGTAGCCCTCT     1260

P   P   L   I   H   N   D   P   E   I   F   D   A   P   K   E   F   R   F   D     414

TTCCTCCACTCATACACAATGACCCGGAAATCTTCGATGCTCCAAAGGAATTTAGGTTCG     1320

R   F   I   E   D   G   K   K   K   S   T   F   F   K   G   G   K   R   L   K     434

ATCGGTTCATAGAAGATGGTAAGAAGAAAAGCACGTTTTTCAAAGGAGGGAAGAGGCTGA     1380

T   Y   V   M   P   F   G   L   G   T   S   K   C   P   G   R   Y   F   A   V     454

AGACTTACGTTATGCCTTTTGGACTCGGAACAAGCAAATGTCCAGGGAGATATTTTGCAG     1440

N   E   M   K   L   L   L   I   E   L   L   T   Y   F   D   L   E   I   I   D     474

TGAACGAAATGAAGCTACTGCTGATTGAGCTTTTAACTTATTTTGATTTAGAAATTATCG     1500

R   K   P   I   G   L   N   H   S   R   M   F   L   G   I   Q   H   P   D   S     494

ACAGGAAGCCTATAGGGCTAAATCACAGTCGGATGTTTTTAGGTATTCAGCACCCCGATT     1560

A   V   S   F   R   Y   K   A   K   S   W   R   S   ***                           507

CTGCCGTCTCCTTTAGGTACAAAGCAAATCTTGGAGAAGCTGAAAGTGTGGCAGAGAAG      1620

CTTTGCAGAGTAAGGCTGCATGTGCTGAGCTCCGTGATTTGGTGCACTCCCCCAAATGCA     1680

ACCGCTACTCTTGTTTGAAAATGGCAAATTTATATTTGGTTGAGATCAATCCAGTTGGTT     1740

TTGGGTCACAAAACCTGTCATAAAATAAAGCAGTGTGATGGtttaaaaaatgtcatggca     1800 atcatttcaggataaggtaaaataacattttcaagtttgtacttactatgattttatca    1860
```

-continued

```
tttgtagtgaatgtgctttt                                              1880
```

SEQ ID NOS 5—6

```
ggatccaaccaagtttccagatcttataaatgtggtgaatggtgaatgacttcctgaaga       60
atggatgaatggatgtgttctagtttggaatcctgtgtcagtcacaagtcaatatgtgac      120
cttgaacatgttattaaatctcccacatccataaaagtgaaaatgctggcattagtggat      180
ttttgccagtgttgaattagacatttatttgtgagtacctgctccatacagtatggtcat      240
ttatttgagttaaaattgttgtatttgaacaaaactcagatgacacctaagcatgaaaaa      300
``` intron 2

```
gctctttatgaagtataaatactcagaaatggaatggcatgttgccaatttgttttctgc      360
tttattgagggaaatatatgagaagtatttaagtcaggggattatgaggaatatttaaag      420
gata(--190nt-)tctagagtgttttccaccatctttcaaaggaaacatgtagtgtacc      680
ttcgaatgaaatggatttgtattaaacttttgccttagttattagggtctttctaattt       740
ttgattaacatatttttttaatttgtggtgtttatttctgttttttattaacaaacgaact     800
```

GlyLysTyrIleThrPheIleProGlyPro
```
catatgctcctctctctttttttttttctGGAAAGTACATAACATTTATACCTGGACCC
```

PheGlnTyrGlnLeuValIleLysAsnHisLysAsnLeuSerPheArgValSerSerAsn
```
TTCCAGTACCAGCTAGTGATAAAAAATCATAAACAATTAAGCTTTCGAGTATCTTCTAAT      920
```

LysLeuSerGluLysAlaPheSerIleSerGlnLeuGlnLysAsnHisAspMetAsnAsp
```
AAATTATCAGAGAAAGCATTTAGCATCAGTCAGTTGCAAAAAAATCATGACATGAATGAT      980
```

GluLeuHisLeuCysTyrGlnPheLeuGlnGLyLysSerLeuAspIleLeuLeuGluSer
```
GAGCTTCACCTCTGCTATCAATTTTTGCAAGGCAAATCTTTGGACATACTCTTGGAAAGC    1040
``` exon 3

MetMetGlnAsnLeuLysGlnValPheGluProGlnLeuLeuLysThrThrSerTrpAsp
```
ATGATGCAGAATCTAAAACAAGTTTTTGAACCCCAGCTGTTAAAAACCACAAGTTGGGAC    1100
```

ThrAlaGluLeuTyrProPheCysSerSerIleIlePheGluIleThrPheThrThrIle
```
ACGGCAGAACTGTATCCATTCTGCAGCTCAATAATATTTGAGATCACATTTACAACTATA    1160
```

TyrGlyLysValIleValCysAspAsnAsnLysPheIleSerGluLeuArgAspAspPhe
```
TATGGAAAAGTTATTGTTTGTGACAACAACAAATTTATTAGTGAGCTAAGAGATGATTTT    1220
```

LeuLysPheAspAspLysPheAlaTyrLeuValSerAsnIleProIleGluLeuLeyGly
```
TTAAAATTTGATGACAAGTTTGCATATTTAGTATCCAACATACCCATTGAGCTTCTAGGA    1280
```

AsnValLysSerIleArgGluKysIleIleLysCysPheSerSerGluLysLeuAlaLys
```
AATGTCAAGTCTATTAGAGAGAAAATTATAAAATGCTTCTCATCAGAAAAGTTAGCCAAG    1340
```

MetGlnGlyTrpSerGluValPheGlnSerArgGlnAspAspLeuGluLysTyrTyrVal
```
ATGCAAGGATGGTCAGAAGTTTTTCAAAGCAGGCAAGATGACCTGGAGAAATATTATGTG    1400
```

HisGluAspLeuGluIleGlyA-
```
CACGAGGACCTTGAAATAGGAGgtaagaacttctgaatgagcacttgcctaaataaaaat    1460
catttacatagacctctgaaataaaaaagacaaaatggcgaccttgaaaatttttttat     1520
gctctttctaattggctaatgataaatgtttactctgatataacctctataattgatatt    1580
ttttttttgctgaggtggtaaacagatacttaatggtgataatgagaaagcgtataact    1640
``` intron 3

```
aagctgcatttatccctcttatctcatccccgaccacaccgccccccccatacacattac    1700
attttaaactattctcattaagcagaaaattagacttcagaagcctattggttctcatta    1760
gcatgcagtgatccttggctggtctgtgtcctaacatcttttaattagcacactgcaaat   1820
```

-laHisHis
```
ctaatcagtgtaataaacgctattaatcttccttt acacttattttctcccaCACATCAT    1880
```

PheGlyPheLeuTrpValSerValAlaSerThrIleProThrMetPheTrpAlaThrTyr
```
TTAGGCTTTCTCTGGGCCTCTGTGGCAAACACTATTCCAACTATGTTCTGGGCAACGTAT    1940
``` exon 4

TyrLeuLeuArgHisProGluAlaMetAlaAlaValArgAspGluIleAspArgLeuLeu
TATCTTCTGCGGCACCCAGAAGCTATGGCAGCAGTGCGTGACGAAATTGACCGTTTGCTG    2000

GlnSerThrGlyGlnLysGluGlySerGlyPheProIleHisLeuThrArgGluGlnLeu
CAGTCAACAGGTCAAAAGGAAGGGTCTGGATTTCCCATCCACCTCACCAGAGAACAATTG    2060

AspSerLeuIleCysLeu
GACAGCCTAATCTGCCTAGgtaattattttatctgttatgaagaagaaggtacctctct    2120 gcaaactcggtttatcactcatagctgtttacaagaggtagaggacacagctgctaattg    2180 acataataactcccatttacatcaattataaattatgtagtttatagccgtagatcatct    2240 intron 4 cattgcatgtaaacataaggcctaxgtaattaactgtgxaaxgtatgxaaaaxxctaacc    2300 aaagctt(--550nt-)cctgactgaacttcttactgccaaagttaaattccataccaat    2960 gagttattctctattctctctgtattgacatttcatctgcggtatcctttagggtacaat    3020 attccaagtttctttagacaaacgcaggaacaaatgttcacatatttctgtttctttatt    3080 cctttgacaagtaggcgagcattttagcctatgttggtctcaaaaaaaatcttttaaata    3140 tgttccaggttctttaatgggacctttcaggagcaaaagtcctcccaggtttggtcaatg    3200 ttcaccctcxgtggccattgaggaaaatgcccxxxxxgttctagagattgttctcacttc    3260 tcaggctaaggcccattgagcaatgccagaaagcatgccttatactagcagtcaatttgg    3320 aagtttgtagtttgtgtctttagcataggttatcaaataaattttatatttxcttttaaa    3380 aaaatctcaacattactaaaatacaaatatccttttattttttctttgcagaattatcggg    3440 gaacaaatccagaaaatttgtgtaaatttcgggtagttgctccacttgatacacagtatt    3500 tctgcatattgtaatttctatgaagatctaggttgcatttcccatacattcaagcagttt    3560 ccattgcattttatgaataagatgacgcatactgggaagtaaggcaaatacactaaaag    3620 gaatatgtgtttgtattctgtatagttattactcttaaaaaaagtagttgtaattcatcc    3680 actcttttactttcaacttttgctattaaaaaatcattttaaatttcagtattaaag    3740 cagaaacatttaaatttattagaccagaaaaataacagattctagaactataatttgaat    3800 ccatttaagcccatagctagagctagagattttcactattggatcc    3846

---

We claim:

1. A DNA molecule selected from the following;
   (a) DNA molecules containing the coding sequence set forth in SEQ ID NO;1 beginning at nucleotide 1 and ending at nucleotide 1242,
   (b) DNA molecules containing the coding sequence set forth in SEQ ID NO:3 beginning at nucleotide 81 and ending at nucleotide 1601,
   (c) DNA molecules comprising a Hippocampal transcript protein coding sequence and which are capable of hybridizing with the DNA molecule defined in (a) or (b) under standard hybridization conditions defined as 2×SSC at 65° C.,
   (d) cytochrome P450-encoding DNA molecules capable of hybridizing with the DNA molecule defined in (a), (b) or (c) under reduced stringency hybridization conditions defined as 2×SSC at 55° C.

2. A DNA molecule according to claim 1 (c) or (d) comprising an Hct-1 gene-associated sequence of another vertebrate species, especially a mammalian species and in particular a human Hct-1 gene-associated sequence.

3. A DNA molecule according to claim 2 selected from the following:
   (e) DNA molecules comprising one or more sequences selected from
      (i) the sequence from position 1 to 830 in SEQ ID NO:5,
      (ii) the sequence from position 831 to 1422 in SEQ ID NO:5, (iii) the sequence from position 1423 to 1872 in SEQ ID NO:5,
(iv) the sequence from position 1873 to 2078 in SEQ ID NO:5, and
(v) the sequence from position 2079 to 3846 in SEQ ID NO:5, and (f) DNA molecules comprising a Hippocampal transcript gene exon or intron sequence and which are capable of hybridizing with the DNA molecules defined in (e) under standard hybridization conditions defined as 2×SSC at 65° C., (g) cytochrome P450-encoding DNA molecules capable of hybridizing with the DNA molecule defined in (e) or (f) under reduced stringency hybridization conditions defined as 6×SSC at 55° C.

4. A DNA molecule comprising a human Hct-1 gene-associated sequence and selected from the following:

(e) DNA molecules comprising one or more sequences selected from
(i) the sequence from position 1 to 830 in SEQ ID NO:5,
(ii) the sequence from position 831 to 1422 in SEQ ID NO:5,
(iii) the sequence from position 1423 to 1872 in SEQ ID NO:5,
(iv) the sequence from position 1873 to 2078 in SEQ ID NO:5, and
(v) the sequence from position 2079 to 3846 in SEQ ID NO:5, and (f) DNA molecules comprising a human Hippocampal transcript gene exon or intron sequence and which are capable of hybridizing with the DNA molecules defined in (e) under standard hybridization conditions defined as 2×SSC at 65° C., (g) cytochrome P450-encoding DNA molecules capable of hybridizing with the DNA molecule defined in (e) or (f) under reduced stringency hybridization conditions defined as 6×SSC at 55° C.

5. A DNA molecule comprising a human Hct-1 gene-associated sequence and selected from the following:

(h) DNA molecules comprising contiguous pairs of sequences selected from
(i) the sequence from position 1 to 830 in SEQ ID NO:5,
(ii) the sequence from position 831 to 1422 in SEQ ID NO:5,
(iii) the sequence from position 1423 to 1872 in SEQ ID NO:5,
(iv) the sequence from position 1873 to 2078 in SEQ ID NO:5, and
(v) the sequence from position 2079 to 3846 in SEQ ID NO:5, and (i) DNA molecules comprising a human Hippocampal transcript gene exon or intron sequence and which are capable of hybridizing with the DNA molecules defined in (h) under standard hybridization conditions defined as 2×SSC at 65° C., (j) cytochrome P450-encoding DNA molecules capable of hybridizing with the DNA molecule defined in (h) or (i) under reduced stringency hybridization conditions defined as 6×SSC at 55° C.

6. A DNA molecule comprising a human Hct-1 gene-associated sequence and selected from the following:

(k) DNA molecules comprising a contiguous coding sequence consisting of the sequences from positions 831 to 1422 and 1873 to 2078 in SEQ ID NO:5, and (l) DNA molecules comprising a Hippocampal transcript gene exon coding sequence and which are capable of hybridizing with the DNA molecules as defined in (k) under standard hybridization conditions defined as 2×SSC at 65° C., (m) cytochrome P450-encoding DNA molecules capable of hybridizing with the DNA molecule defined in (k) or (l) under reduced stringency hybridization conditions defined as 6×SSC at 55° C.

7. A DNA molecule encoding an Hct-1 gene-associated coding sequence coded for by a DNA molecule as claimed in claim 1, but which differs in sequence from the sequences of the DNA molecules claimed in claims 1 to 6 by virtue of one or more amino acids of said Hct-1 gene-associated sequences being encoded by degenerate codons.

8. A DNA molecule consisting of a contiguous sequence of at least 18 nucleotides from the DNA sequence set forth in SEQ ID NOS:1, 3 and 5.

9. A DNA sequence according to claim 8 containing at least 24 and most preferably at least 30 nucleotide taken from said sequence.

10. A process for producing a Hct-1 polypeptide, which comprises culturing a transformed host and recovering the desired Hct-1 polypeptide, characterised in that the host is transformed with nucleic acid comprising a coding sequence as defined in claim 1.

11. A process according to claim 10 wherein the transformed host cell is a yeast, bacterial, insect or mammalian cell.

12. A process according to claim 10 wherein the nucleic acid comprises an expression construct or an expression vector.

13. A process according to claim 12 wherein the vector is a vaccinia virus or baculovirus vector, a yeast plasmid or integration vector.

* * * * *

UNITED STATES PATENT AND TRADEMARK OFFICE
CERTIFICATE OF CORRECTION

PATENT NO. : 5,976,850
DATED : November 2, 1999
INVENTOR(S) : LATHE et al

It is certified that error appears in the above-identified patent and that said Letters Patent is hereby corrected as shown below:

On the title page item [73], delete "University of Edinburgh, Edinburgh," and replace by --BTG International Limited, London,--.

Signed and Sealed this

Eighteenth Day of July, 2000

*Attest:*

Q. TODD DICKINSON

*Attesting Officer*     *Director of Patents and Trademarks*

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
        (A) LENGTH: 1763 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: rat (ix) FEATURE:
        (A) NAME/KEY: CDS
        (B) LOCATION: 1..1242

(xi) SEQUENCE DESCRIPTION: SEQ ID NO:1:

```
GCC TTG GAG TAC CAG TAT GTA ATG AAA AAC CCA AAA CAA TTA AGC TTT        48
Ala Leu Glu Tyr Gln Tyr Val Met Lys Asn Pro Lys Gln Leu Ser Phe
 1               5                  10                  15

GAG AAG TTC AGC CGA AGA TTA TCA GCG AAA GCC TTC TCT GTC AAG AAG        96
Glu Lys Phe Ser Arg Arg Leu Ser Ala Lys Ala Phe Ser Val Lys Lys
             20                  25                  30

CTG CTA ACT AAT GAC GAC CTT AGC AAT GAC ATT CAC AGA GGC TAT CTT       144
Leu Leu Thr Asn Asp Asp Leu Ser Asn Asp Ile His Arg Gly Tyr Leu
         35                  40                  45

CTT TTA CAA GGC AAA TCT CTG GAT GGT CTT CTG GAA ACC ATG ATC CAA       192
Leu Leu Gln Gly Lys Ser Leu Asp Gly Leu Leu Glu Thr Met Ile Gln
     50                  55                  60

GAA GTA AAA GAA ATA TTT GAG TCC AGA CTG CTA AAA CTC ACA GAT TGG       240
Glu Val Lys Glu Ile Phe Glu Ser Arg Leu Leu Lys Leu Thr Asp Trp
 65                  70                  75                  80

AAT ACA GCA AGA GTA TTT GAT TTC TGT AGT TCA CTG GTA TTT GAA ATC       288
Asn Thr Ala Arg Val Phe Asp Phe Cys Ser Ser Leu Val Phe Glu Ile
                 85                  90                  95

ACA TTT ACA ACT ATA TAT GGA AAA ATT CTT GCT GCT AAC AAA AAA CAA       336
Thr Phe Thr Thr Ile Tyr Gly Lys Ile Leu Ala Ala Asn Lys Lys Gln
            100                 105                 110

ATT ATC AGT GAG CTG AGG GAT GAT TTT TTA AAA TTT GAT GAC CAT TTC       384
Ile Ile Ser Glu Leu Arg Asp Asp Phe Leu Lys Phe Asp Asp His Phe
        115                 120                 125

CCA TAC TTA GTA TCT GAC ATA CCT ATT CAG CTT CTA AGA AAT GCA GAA       432
Pro Tyr Leu Val Ser Asp Ile Pro Ile Gln Leu Leu Arg Asn Ala Glu
    130                 135                 140

TTT ATG CAG AAG AAA ATT ATA AAA TGT CTC ACA CCA GAA AAA GTA GCT       480
Phe Met Gln Lys Lys Ile Ile Lys Cys Leu Thr Pro Glu Lys Val Ala
145                 150                 155                 160

CAG ATG CAA AGA CGG TCA GAA ATT GTT CAG GAG AGG CAG GAG ATG CTG       528
Gln Met Gln Arg Arg Ser Glu Ile Val Gln Glu Arg Gln Glu Met Leu
                165                 170                 175

AAA AAA TAC TAC GGG CAT GAA GAG TTT GAA ATA GGA GCA CAT CAT CTT       576
Lys Lys Tyr Tyr Gly His Glu Glu Phe Glu Ile Gly Ala His His Leu
            180                 185                 190

GGC TTG CTC TGG GCC TCT CTA GCA AAC ACC ATT CCA GCT ATG TTC TGG       624
Gly Leu Leu Trp Ala Ser Leu Ala Asn Thr Ile Pro Ala Met Phe Trp
        195                 200                 205

GCA ATG TAT TAT CTT CTT CAG CAT CCA GAA GCT ATG GAA GTC CTG CGT       672
Ala Met Tyr Tyr Leu Leu Gln His Pro Glu Ala Met Glu Val Leu Arg
    210                 215                 220

GAC GAA ATT GAC AGC TTC CTG CAG TCA ACA GGT CAA AAG AAA GGA CCT       720
Asp Glu Ile Asp Ser Phe Leu Gln Ser Thr Gly Gln Lys Lys Gly Pro
225                 230                 235                 240

GGA ATT TCT GTC CAC TTC ACC AGA GAA CAA TTG GAC AGC TTG GTC TGC       768
Gly Ile Ser Val His Phe Thr Arg Glu Gln Leu Asp Ser Leu Val Cys
                245                 250                 255

CTG GAA AGC GCT ATT CTT GAG GTT CTG AGG TTG TGC TCC TAC TCC AGC       816
Leu Glu Ser Ala Ile Leu Glu Val Leu Arg Leu Cys Ser Tyr Ser Ser
            260                 265                 270

ATC ATC CGT GAA GTG CAA GAG GAT ATG GAT TTC AGC TCA GAG AGT AGG       864
Ile Ile Arg Glu Val Gln Glu Asp Met Asp Phe Ser Ser Glu Ser Arg
        275                 280                 285

AGC TAC CGT CTG CGG AAA GGA GAC TTT GTA GCT GTC TTT CCT CCA ATG       912
Ser Tyr Arg Leu Arg Lys Gly Asp Phe Val Ala Val Phe Pro Pro Met
    290                 295                 300

ATA CAC AAT GAC CCA GAA GTC TTC GAT GCT CCA AAG GAC TTT AGG TTT       960
Ile His Asn Asp Pro Glu Val Phe Asp Ala Pro Lys Asp Phe Arg Phe
305                 310                 315                 320
```

-continued

```
GAT CGC TTC GTA GAA GAT GGT AAG AAG AAA ACA ACG TTT TTC AAA GGA      1008
Asp Arg Phe Val Glu Asp Gly Lys Lys Lys Thr Thr Phe Phe Lys Gly
                325                 330                 335

GGA AAA AAG CTG AAG AGT TAC ATT ATA CCA TTT GGA CTT GGA ACA AGC      1056
Gly Lys Lys Leu Lys Ser Tyr Ile Ile Pro Phe Gly Leu Gly Thr Ser
            340                 345                 350

AAA TGT CCA GGC AGA TAC TTT GCA ATT AAT GAA ATG AAG CTA CTA GTG      1104
Lys Cys Pro Gly Arg Tyr Phe Ala Ile Asn Glu Met Lys Leu Leu Val
        355                 360                 365

ATT ATA CTT TTA ACT TAT TTT GAT TTA GAA GTC ATT GAC ACT AAG CCT      1152
Ile Ile Leu Leu Thr Tyr Phe Asp Leu Glu Val Ile Asp Thr Lys Pro
    370                 375                 380

ATA GGA CTA AAC CAC AGT CGC ATG TTT CTG GGC ATT CAG CAT CCA GAC      1200
Ile Gly Leu Asn His Ser Arg Met Phe Leu Gly Ile Gln His Pro Asp
385                 390                 395                 400

TCT GAC ATC TCA TTT AGG TAC AAG GCA AAA TCT TGG AGA TCC              1242
Ser Asp Ile Ser Phe Arg Tyr Lys Ala Lys Ser Trp Arg Ser
                405                 410

TGAAAGGGTG GCAGAGAAGC TTAGCGGAAT AAGGCTGCAC ATGCTGAGCT CTGTGATTTG    1302

CTGTACTCCC CAAATGCAGC CACTATTCTT GTTTGTTAGA AAATGGCAAA TTTTTATTTG    1362

ATTGCGATCC ATCCAGTTTG TTTTGGGTCA CAAAACCTGT CATAAAATAA AGCGCTGTCA    1422

TGGTGTAAAA AAATGTCATG GCAATCATTT CAGGATAAGG TAAAATAACG TTTTCAAGTT    1482

TGTACTTACT ATGATTTTTA TCATTTGTAG TGAATGTGCT TTTCCAGTAA TAAATTTGCG    1542

CCAGGGTGAT TTTTTTTAAT TACTGAAATC CTCTAATATC GGTTTTATGT GCTGCCAGAA    1602

AACTCTGCCA TCAATGGACA GTATAACAAT TTCCAGTTTT CCAGAGAAGG GAGAAATTAA    1662

GCCCCATGAG TTACGCTGTA TAAAATTGTT CTCTTCAACT ATAATATCAA TAATGTCTAT    1722

ATCACCAGGT TACCTTTGCA TTAAATCGAG TTTTGCAAAA G                       1763
```

(2) INFORMATION FOR SEQ ID NO:2:

(i) SEQUENCE CHARACTERISTICS:
        (A) LENGTH: 414 amino acids
        (B) TYPE: amino acid
        (D) TOPOLOGY: linear (ii) MOLECULE TYPE: protein (xi) SEQUENCE DESCRIPTION: SEQ ID NO:2:

```
Ala Leu Glu Tyr Gln Tyr Val Met Lys Asn Pro Lys Gln Leu Ser Phe
1               5                   10                  15

Glu Lys Phe Ser Arg Arg Leu Ser Ala Lys Ala Phe Ser Val Lys Lys
                20                  25                  30

Leu Leu Thr Asn Asp Asp Leu Ser Asn Asp Ile His Arg Gly Tyr Leu
            35                  40                  45

Leu Leu Gln Gly Lys Ser Leu Asp Gly Leu Leu Glu Thr Met Ile Gln
        50                  55                  60

Glu Val Lys Glu Ile Phe Glu Ser Arg Leu Leu Lys Leu Thr Asp Trp
65                  70                  75                  80

Asn Thr Ala Arg Val Phe Asp Phe Cys Ser Ser Leu Val Phe Glu Ile
                85                  90                  95

Thr Phe Thr Thr Ile Tyr Gly Lys Ile Leu Ala Ala Asn Lys Lys Gln
            100                 105                 110

Ile Ile Ser Glu Leu Arg Asp Asp Phe Leu Lys Phe Asp Asp His Phe
        115                 120                 125

Pro Tyr Leu Val Ser Asp Ile Pro Ile Gln Leu Leu Arg Asn Ala Glu
    130                 135                 140
```

```
Phe Met Gln Lys Lys Ile Ile Lys Cys Leu Thr Pro Glu Lys Val Ala
145                 150                 155                 160

Gln Met Gln Arg Arg Ser Glu Ile Val Gln Glu Arg Gln Glu Met Leu
            165                 170                 175

Lys Lys Tyr Tyr Gly His Glu Phe Glu Ile Gly Ala His His Leu
        180                 185                 190

Gly Leu Leu Trp Ala Ser Leu Ala Asn Thr Ile Pro Ala Met Phe Trp
        195                 200                 205

Ala Met Tyr Tyr Leu Leu Gln His Pro Glu Ala Met Glu Val Leu Arg
210                 215                 220

Asp Glu Ile Asp Ser Phe Leu Gln Ser Thr Gly Gln Lys Lys Gly Pro
225                 230                 235                 240

Gly Ile Ser Val His Phe Thr Arg Glu Gln Leu Asp Ser Leu Val Cys
                245                 250                 255

Leu Glu Ser Ala Ile Leu Glu Val Leu Arg Leu Cys Ser Tyr Ser Ser
            260                 265                 270

Ile Ile Arg Glu Val Gln Glu Asp Met Asp Phe Ser Ser Glu Ser Arg
            275                 280                 285

Ser Tyr Arg Leu Arg Lys Gly Asp Phe Val Ala Val Phe Pro Pro Met
290                 295                 300

Ile His Asn Asp Pro Glu Val Phe Asp Ala Pro Lys Asp Phe Arg Phe
305                 310                 315                 320

Asp Arg Phe Val Glu Asp Gly Lys Lys Lys Thr Thr Phe Phe Lys Gly
                325                 330                 335

Gly Lys Lys Leu Lys Ser Tyr Ile Ile Pro Phe Gly Leu Gly Thr Ser
            340                 345                 350

Lys Cys Pro Gly Arg Tyr Phe Ala Ile Asn Glu Met Lys Leu Leu Val
            355                 360                 365

Ile Ile Leu Leu Thr Tyr Phe Asp Leu Glu Val Ile Asp Thr Lys Pro
            370                 375                 380

Ile Gly Leu Asn His Ser Arg Met Phe Leu Gly Ile Gln His Pro Asp
385                 390                 395                 400

Ser Asp Ile Ser Phe Arg Tyr Lys Ala Lys Ser Trp Arg Ser
                405                 410

(2) INFORMATION FOR SEQ ID NO:3:

(i) SEQUENCE CHARACTERISTICS:
        (A) LENGTH: 1880 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: mouse (ix) FEATURE:
        (A) NAME/KEY: CDS
        (B) LOCATION: 81..1601

(xi) SEQUENCE DESCRIPTION: SEQ ID NO:3:

GGCAGGCACA GCCTCTGGTC TAAGAAGAGA GGGCACTGTG CAAAAGCCAT CGCTCCCTAC        60

AGAGCCGCCA GCTCGTCGGG ATG CAG GGA GCC ACG ACC CTA GAT GCC GCC          110
               Met Gln Gly Ala Thr Thr Leu Asp Ala Ala
                 1               5                  10

TCG CCA GGG CCT CTC GCC CTC CTA GGC CTT CTC TTT GCC GCC ACC TTA        158
Ser Pro Gly Pro Leu Ala Leu Leu Gly Leu Leu Phe Ala Ala Thr Leu
```

```
                       15                   20                      25
CTG CTC TCG GCC CTG TTC CTC CTC ACC CGG CGC ACC AGG CGC CCT CGT         206
Leu Leu Ser Ala Leu Phe Leu Leu Thr Arg Arg Thr Arg Arg Pro Arg
                 30                      35              40

GAA CCA CCC TTG ATA AAA GGT TGG CTT CCT TAT CTT GGC ATG GCC CTG         254
Glu Pro Pro Leu Ile Lys Gly Trp Leu Pro Tyr Leu Gly Met Ala Leu
             45                      50                  55

AAA TTC TTT AAG GAT CCG TTA ACT TTC TTG AAA ACT CTT CAA AGG CAA         302
Lys Phe Phe Lys Asp Pro Leu Thr Phe Leu Lys Thr Leu Gln Arg Gln
         60                      65                  70

CAT GGT GAC ACT TTC ACT GTC TTC CTT GTG GGG AAG TAT ATA ACA TTT         350
His Gly Asp Thr Phe Thr Val Phe Leu Val Gly Lys Tyr Ile Thr Phe
75                       80                  85                  90

GTT CTG AAC CCT TTC CAG TAC CAG TAT GTA ACG AAA AAC CCA AAA CAA         398
Val Leu Asn Pro Phe Gln Tyr Gln Tyr Val Thr Lys Asn Pro Lys Gln
                     95                     100             105

TTA AGC TTT CAG AAG TTC AGC AGC CGA TTA TCA GCG AAA GCC TTC TCT         446
Leu Ser Phe Gln Lys Phe Ser Ser Arg Leu Ser Ala Lys Ala Phe Ser
                 110                     115             120

GTA AAG AAG CTG CTT ACT GAT GAC GAC CTT AAT GAA GAC GTT CAC AGA         494
Val Lys Lys Leu Leu Thr Asp Asp Asp Leu Asn Glu Asp Val His Arg
             125                     130                 135

GCC TAT CTA CTT CTA CAA GGC AAA CCT TTG GAT GCT CTT CTG GAA ACT         542
Ala Tyr Leu Leu Leu Gln Gly Lys Pro Leu Asp Ala Leu Leu Glu Thr
        140                     145                  150

ATG ATC CAA GAA GTA AAA GAA TTA TTT GAG TCC CAA CTG CTA AAA ATC         590
Met Ile Gln Glu Val Lys Glu Leu Phe Glu Ser Gln Leu Leu Lys Ile
155                      160                  165                 170

ACA GAT TGG AAC ACA GAA AGA ATA TTT GCA TTC TGT GGC TCA CTG GTA         638
Thr Asp Trp Asn Thr Glu Arg Ile Phe Ala Phe Cys Gly Ser Leu Val
                 175                     180                 185

TTT GAG ATC ACA TTT GCG ACT CTA TAT GGA AAA ATT CTT GCT GGT AAC         686
Phe Glu Ile Thr Phe Ala Thr Leu Tyr Gly Lys Ile Leu Ala Gly Asn
             190                     195                 200

AAG AAA CAA ATT ATC AGT GAG CTA AGG GAT GAT TTT TTT AAA TTT GAT         734
Lys Lys Gln Ile Ile Ser Glu Leu Arg Asp Asp Phe Phe Lys Phe Asp
         205                     210                 215

GAC ATG TTC CCA TAC TTA GTA TCT GAC ATA CCT ATT CAG CTT CTA AGA         782
Asp Met Phe Pro Tyr Leu Val Ser Asp Ile Pro Ile Gln Leu Leu Arg
    220                      225                 230

AAT GAA GAA TCT ATG CAG AAG AAA ATT ATA AAA TGC CTC ACA TCA GAA         830
Asn Glu Glu Ser Met Gln Lys Lys Ile Ile Lys Cys Leu Thr Ser Glu
235                      240                  245                 250

AAA GTA GCT CAG ATG CAA GGA CAG TCA AAA ATT GTT CAG GAA AGC CAA         878
Lys Val Ala Gln Met Gln Gly Gln Ser Lys Ile Val Gln Glu Ser Gln
                 255                     260                 265

GAT CTG CTG AAA AGA TAC TAT AGG CAT GAC GAT TCT GAA ATA GGA GCA         926
Asp Leu Leu Lys Arg Tyr Tyr Arg His Asp Asp Ser Glu Ile Gly Ala
             270                     275                 280

CAT CAT CTT GGC TTT CTC TGG GCC TCT CTA GCA AAC ACC ATT CCA GCT         974
His His Leu Gly Phe Leu Trp Ala Ser Leu Ala Asn Thr Ile Pro Ala
         285                     290                 295

ATG TTC TGG GCA ATG TAT TAT ATT CTT CGG CAT CCT GAA GCT ATG GAA        1022
Met Phe Trp Ala Met Tyr Tyr Ile Leu Arg His Pro Glu Ala Met Glu
    300                      305                 310

GCC CTG CGT GAC GAA ATT GAC AGT TTC CTG CAG TCA ACA GGT CAA AAG        1070
Ala Leu Arg Asp Glu Ile Asp Ser Phe Leu Gln Ser Thr Gly Gln Lys
315                      320                  325                 330

AAA GGG CCT GGA ATT TCA GTC CAC TTC ACC AGA GAA CAA TTG GAC AGC        1118
Lys Gly Pro Gly Ile Ser Val His Phe Thr Arg Glu Gln Leu Asp Ser
```

```
                        335                  340                      345
TTG GTC TGC CTG GAA AGC ACT ATT CTT GAG GTT CTG AGG CTG TGC TCA         1166
Leu Val Cys Leu Glu Ser Thr Ile Leu Glu Val Leu Arg Leu Cys Ser
            350                      355                  360

TAC TCC AGC ATC ATC CGA GAA GTG CAG GAG GAT ATG AAT CTC AGC TTA         1214
Tyr Ser Ser Ile Ile Arg Glu Val Gln Glu Asp Met Asn Leu Ser Leu
        365                      370                  375

GAG AGT AAG AGT TTC TCT CTG CGG AAA GGA GAT TTT GTA GCC CTC TTT         1262
Glu Ser Lys Ser Phe Ser Leu Arg Lys Gly Asp Phe Val Ala Leu Phe
            380                      385                  390

CCT CCA CTC ATA CAC AAT GAC CCG GAA ATC TTC GAT GCT CCA AAG GAA         1310
Pro Pro Leu Ile His Asn Asp Pro Glu Ile Phe Asp Ala Pro Lys Glu
395                     400                      405                  410

TTT AGG TTC GAT CGG TTC ATA GAA GAT GGT AAG AAG AAA AGC ACG TTT         1358
Phe Arg Phe Asp Arg Phe Ile Glu Asp Gly Lys Lys Lys Ser Thr Phe
                415                      420                  425

TTC AAA GGA GGG AAG AGG CTG AAG ACT TAC GTT ATG CCT TTT GGA CTC         1406
Phe Lys Gly Gly Lys Arg Leu Lys Thr Tyr Val Met Pro Phe Gly Leu
            430                      435                  440

GGA ACA AGC AAA TGT CCA GGG AGA TAT TTT GCA GTG AAC GAA ATG AAG         1454
Gly Thr Ser Lys Cys Pro Gly Arg Tyr Phe Ala Val Asn Glu Met Lys
            445                      450                  455

CTA CTG CTG ATT GAG CTT TTA ACT TAT TTT GAT TTA GAA ATT ATC GAC         1502
Leu Leu Leu Ile Glu Leu Leu Thr Tyr Phe Asp Leu Glu Ile Ile Asp
460                     465                      470

AGG AAG CCT ATA GGG CTA AAT CAC AGT CGG ATG TTT TTA GGT ATT CAG         1550
Arg Lys Pro Ile Gly Leu Asn His Ser Arg Met Phe Leu Gly Ile Gln
475                     480                      485                  490

CAC CCC GAT TCT GCC GTC TCC TTT AGG TAC AAA GCA AAA TCT TGG AGA         1598
His Pro Asp Ser Ala Val Ser Phe Arg Tyr Lys Ala Lys Ser Trp Arg
                495                      500                  505

AGC TGAAAGTGTG GCAGAGAAGC TTTGCAGAGT AAGGCTGCAT GTGCTGAGCT              1651
Ser

CCGTGATTTG GTGCACTCCC CCAAATGCAA CCGCTACTCT TGTTTGAAAA TGGCAAATTT       1711

ATATTTGGTT GAGATCAATC CAGTTGGTTT TGGGTCACAA AACCTGTCAT AAAATAAAGC       1771

AGTGTGATGG TTTAAAAAAT GTCATGGCAA TCATTTCAGG ATAAGGTAAA ATAACATTTT       1831

CAAGTTTGTA CTTACTATGA TTTTTATCAT TTGTAGTGAA TGTGCTTTTT                  1880

(2) INFORMATION FOR SEQ ID NO:4:

(i) SEQUENCE CHARACTERISTICS:
        (A) LENGTH: 507 amino acids
        (B) TYPE: amino acid
        (D) TOPOLOGY: linear (ii) MOLECULE TYPE: protein (xi) SEQUENCE DESCRIPTION: SEQ ID NO:4:

Met Gln Gly Ala Thr Thr Leu Asp Ala Ala Ser Pro Gly Pro Leu Ala
1               5                   10                  15

Leu Leu Gly Leu Leu Phe Ala Ala Thr Leu Leu Ser Ala Leu Phe
            20                  25                  30

Leu Leu Thr Arg Arg Thr Arg Arg Pro Arg Glu Pro Pro Leu Ile Lys
        35                  40                  45

Gly Trp Leu Pro Tyr Leu Gly Met Ala Leu Lys Phe Lys Asp Pro
    50                  55                  60

Leu Thr Phe Leu Lys Thr Leu Gln Arg Gln His Gly Asp Thr Phe Thr
65                  70                  75                  80
```

-continued

```
Val Phe Leu Val Gly Lys Tyr Ile Thr Phe Val Leu Asn Pro Phe Gln
                 85                  90                  95

Tyr Gln Tyr Val Thr Lys Asn Pro Lys Gln Leu Ser Phe Gln Lys Phe
            100                 105                 110

Ser Ser Arg Leu Ser Ala Lys Ala Phe Ser Val Lys Lys Leu Leu Thr
            115                 120                 125

Asp Asp Asp Leu Asn Glu Asp Val His Arg Ala Tyr Leu Leu Leu Gln
            130                 135                 140

Gly Lys Pro Leu Asp Ala Leu Leu Glu Thr Met Ile Gln Glu Val Lys
145                 150                 155                 160

Glu Leu Phe Glu Ser Gln Leu Leu Lys Ile Thr Asp Trp Asn Thr Glu
                165                 170                 175

Arg Ile Phe Ala Phe Cys Gly Ser Leu Val Phe Glu Ile Thr Phe Ala
                180                 185                 190

Thr Leu Tyr Gly Lys Ile Leu Ala Gly Asn Lys Lys Gln Ile Ile Ser
            195                 200                 205

Glu Leu Arg Asp Asp Phe Phe Lys Phe Asp Asp Met Phe Pro Tyr Leu
            210                 215                 220

Val Ser Asp Ile Pro Ile Gln Leu Leu Arg Asn Glu Glu Ser Met Gln
225                 230                 235                 240

Lys Lys Ile Ile Lys Cys Leu Thr Ser Glu Lys Val Ala Gln Met Gln
                245                 250                 255

Gly Gln Ser Lys Ile Val Gln Glu Ser Gln Asp Leu Leu Lys Arg Tyr
            260                 265                 270

Tyr Arg His Asp Asp Ser Glu Ile Gly Ala His His Leu Gly Phe Leu
            275                 280                 285

Trp Ala Ser Leu Ala Asn Thr Ile Pro Ala Met Phe Trp Ala Met Tyr
            290                 295                 300

Tyr Ile Leu Arg His Pro Glu Ala Met Glu Ala Leu Arg Asp Glu Ile
305                 310                 315                 320

Asp Ser Phe Leu Gln Ser Thr Gly Gln Lys Lys Gly Pro Gly Ile Ser
            325                 330                 335

Val His Phe Thr Arg Glu Gln Leu Asp Ser Leu Val Cys Leu Glu Ser
            340                 345                 350

Thr Ile Leu Glu Val Leu Arg Leu Cys Ser Tyr Ser Ser Ile Ile Arg
            355                 360                 365

Glu Val Gln Glu Asp Met Asn Leu Ser Leu Glu Ser Lys Ser Phe Ser
            370                 375                 380

Leu Arg Lys Gly Asp Phe Val Ala Leu Phe Pro Pro Leu Ile His Asn
385                 390                 395                 400

Asp Pro Glu Ile Phe Asp Ala Pro Lys Glu Phe Arg Phe Asp Arg Phe
            405                 410                 415

Ile Glu Asp Gly Lys Lys Lys Ser Thr Phe Phe Lys Gly Gly Lys Arg
            420                 425                 430

Leu Lys Thr Tyr Val Met Pro Phe Gly Leu Gly Thr Ser Lys Cys Pro
            435                 440                 445

Gly Arg Tyr Phe Ala Val Asn Glu Met Lys Leu Leu Leu Ile Glu Leu
            450                 455                 460

Leu Thr Tyr Phe Asp Leu Glu Ile Ile Asp Arg Lys Pro Ile Gly Leu
465                 470                 475                 480

Asn His Ser Arg Met Phe Leu Gly Ile Gln His Pro Asp Ser Ala Val
            485                 490                 495

Ser Phe Arg Tyr Lys Ala Lys Ser Trp Arg Ser
            500                 505
```

(2) INFORMATION FOR SEQ ID NO:5:

(i) SEQUENCE CHARACTERISTICS:
        (A) LENGTH: 3846 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: human (ix) FEATURE:
        (A) NAME/KEY: CDS
        (B) LOCATION: join(831..1422, 1873..2078)

(ix) FEATURE:
        (A) NAME/KEY: intron
        (B) LOCATION: 1..830

(ix) FEATURE:
        (A) NAME/KEY: exon
        (B) LOCATION: 831..1422

(ix) FEATURE:
        (A) NAME/KEY: intron
        (B) LOCATION: 1423..1872

(ix) FEATURE:
        (A) NAME/KEY: exon
        (B) LOCATION: 1873..2078

(ix) FEATURE:
        (A) NAME/KEY: intron
        (B) LOCATION: 2079..3846

(xi) SEQUENCE DESCRIPTION: SEQ ID NO:5:

```
GGATCCAACC AAGTTTCCAG ATCTTATAAA TGTGGTGAAT GGTGAATGAC TTCCTGAAGA      60

ATGGATGAAT GGATGTGTTC TAGTTTGGAA TCCTGTGTCA GTCACAAGTC AATATGTGAC     120

CTTGAACATG TTATTAAATC TCCCACATCC ATAAAAGTGA AAATGCTGGC ATTAGTGGAT     180

TTTTGCCAGT GTTGAATTAG ACATTTATTT GTGAGTACCT GCTCCATACA GTATGGTCAT     240

TTATTTGAGT TAAAATTGTT GTATTTGAAC AAAACTCAGA TGACACCTAA GCATGAAAAA     300

GCTCTTTATG AAGTATAAAT ACTCAGAAAT GGAATGGCAT GTTGCCAATT TGTTTTCTGC     360

TTTATTGAGG GAAATATATG AGAAGTATTT AAGTCAGGGG ATTATGAGGA ATATTTAAAG     420

GATANNNNNN NNNNNNNNNN NNNNNNNNNN NNNNNNNNNN NNNNNNNNNN NNNNNNNNNN     480

NNNNNNNNNN NNNNNNNNNN NNNNNNNNNN NNNNNNNNNN NNNNNNNNNN NNNNNNNNNN     540

NNNNNNNNNN NNNNNNNNNN NNNNNNNNNN NNNNNNNNNN NNNNNNNNNN NNNNNNNNNN     600

NNNNNNNNNN NNNNNNNNNN NNNNNNNNNN NNNNTCTAGA GTGTTTTCCA CCATCTTTCA     660

AAGGAAACAT GTAGTGTACC TTCGAATGAA ATGGATTTGT ATTAAACTTT TTGCCTTAGT     720

TATTAGGGTC TTTCTAATTT TGATTAACA TATTTTTTA ATTTGTGGTG TTTATTTCTG      780

TTTTTATTAA CAAACGAACT CATATGCTCC TCTCTCTTTT TTTTTTTTCT GGA AAG       836
                                                       Gly Lys
                                                         1

TAC ATA ACA TTT ATA CCT GGA CCC TTC CAG TAC CAG CTA GTG ATA AAA      884
Tyr Ile Thr Phe Ile Pro Gly Pro Phe Gln Tyr Gln Leu Val Ile Lys
         5                  10                  15

AAT CAT AAA CAA TTA AGC TTT CGA GTA TCT TCT AAT AAA TTA TCA GAG      932
Asn His Lys Gln Leu Ser Phe Arg Val Ser Ser Asn Lys Leu Ser Glu
     20                  25                  30

AAA GCA TTT AGC ATC AGT CAG TTG CAA AAA AAT CAT GAC ATG AAT GAT      980
```

```
                Lys Ala Phe Ser Ile Ser Gln Leu Gln Lys Asn His Asp Met Asn Asp
                 35                  40                  45                  50

GAG CTT CAC CTC TGC TAT CAA TTT TTG CAA GGC AAA TCT TTG GAC ATA              1028
Glu Leu His Leu Cys Tyr Gln Phe Leu Gln Gly Lys Ser Leu Asp Ile
                     55                  60                  65

CTC TTG GAA AGC ATG ATG CAG AAT CTA AAA CAA GTT TTT GAA CCC CAG              1076
Leu Leu Glu Ser Met Met Gln Asn Leu Lys Gln Val Phe Glu Pro Gln
             70                  75                  80

CTG TTA AAA ACC ACA AGT TGG GAC ACG GCA GAA CTG TAT CCA TTC TGC              1124
Leu Leu Lys Thr Thr Ser Trp Asp Thr Ala Glu Leu Tyr Pro Phe Cys
         85                  90                  95

AGC TCA ATA ATA TTT GAG ATC ACA TTT ACA ACT ATA TAT GGA AAA GTT              1172
Ser Ser Ile Ile Phe Glu Ile Thr Phe Thr Thr Ile Tyr Gly Lys Val
     100                 105                 110

ATT GTT TGT GAC AAC AAC AAA TTT ATT AGT GAG CTA AGA GAT GAT TTT              1220
Ile Val Cys Asp Asn Asn Lys Phe Ile Ser Glu Leu Arg Asp Asp Phe
115                 120                 125                 130

TTA AAA TTT GAT GAC AAG TTT GCA TAT TTA GTA TCC AAC ATA CCC ATT              1268
Leu Lys Phe Asp Asp Lys Phe Ala Tyr Leu Val Ser Asn Ile Pro Ile
                 135                 140                 145

GAG CTT CTA GGA AAT GTC AAG TCT ATT AGA GAG AAA ATT ATA AAA TGC              1316
Glu Leu Leu Gly Asn Val Lys Ser Ile Arg Glu Lys Ile Ile Lys Cys
             150                 155                 160

TTC TCA TCA GAA AAG TTA GCC AAG ATG CAA GGA TGG TCA GAA GTT TTT              1364
Phe Ser Ser Glu Lys Leu Ala Lys Met Gln Gly Trp Ser Glu Val Phe
         165                 170                 175

CAA AGC AGG CAA GAT GAC CTG GAG AAA TAT TAT GTG CAC GAG GAC CTT              1412
Gln Ser Arg Gln Asp Asp Leu Glu Lys Tyr Tyr Val His Glu Asp Leu
     180                 185                 190

GAA ATA GGA G GTAAGAACTT CTGAATGAGC ACTTGCCTAA ATAAAAATCA                    1462
Glu Ile Gly
195

TTTACATAGA CCTCTGAAAT AAAAAAAGAC AAAATGGCGA CCTTGAAAAT TTTTTTATGC            1522

TCTTTCTAAT TGGCTAATGA TAAATGTTTA CTCTGATATA ACCTCTATAA TTGATATTTT            1582

TTTTTTTGCT GAGGTGGTAA ACAGATACTT AATGGTGATA ATGAGAAAGC GTATAACTAA            1642

GCTGCATTTA TCCCTCTTAT CTCATCCCCG ACCACACCGC CCCCCCCATA CACATTACAT            1702

TTTAAACTAT TCTCATTAAG CAGAAAATTA GACTTCAGAA GCCTATTGGT TCTCATTAGC            1762

ATGCAGTGAT CCTTGGCTGG TCTGTGTCCT AACATCTTTT AATTAGCACA CTGCAAATCT            1822

AATCAGTGTA ATAACGCTA TTAATCTTCC TTTACACTTA TTTTCTCCCA    CA CAT              1877
                                                            Ala His

CAT TTA GGC TTT CTC TGG GCC TCT GTG GCA AAC ACT ATT CCA ACT ATG              1925
His Leu Gly Phe Leu Trp Ala Ser Val Ala Asn Thr Ile Pro Thr Met
200                 205                 210                 215

TTC TGG GCA ACG TAT TAT CTT CTG CGG CAC CCA GAA GCT ATG GCA GCA              1973
Phe Trp Ala Thr Tyr Tyr Leu Leu Arg His Pro Glu Ala Met Ala Ala
                 220                 225                 230

GTG CGT GAC GAA ATT GAC CGT TTG CTG CAG TCA ACA GGT CAA AAG GAA              2021
Val Arg Asp Glu Ile Asp Arg Leu Leu Gln Ser Thr Gly Gln Lys Glu
             235                 240                 245

GGG TCT GGA TTT CCC ATC CAC CTC ACC AGA GAA CAA TTG GAC AGC CTA              2069
Gly Ser Gly Phe Pro Ile His Leu Thr Arg Glu Gln Leu Asp Ser Leu
         250                 255                 260

ATC TGC CTA GGTAATTATT TTATCTGTTA TGAAGAAAGA AGGTACCTCT                      2118
Ile Cys Leu
     265

CTGCAAACTC GGTTTATCAC TCATAGCTGT TTACAAGAGG TAGAGGACAC AGCTGCTAAT            2178
```

```
TGACATAATA ACTCCCATTT ACATCAATTA TAAATTATGT AGTTTATAGC CGTAGATCAT       2238

CTCATTGCAT GTAAACATAA GGCCTANGTA ATTAACTGTG NAANGTATGN AAAANNCTAA       2298

CCAAAGCTTN NNNNNNNNNN NNNNNNNNNN NNNNNNNNNN NNNNNNNNNN NNNNNNNNNN       2358

NNNNNNNNNN NNNNNNNNNN NNNNNNNNNN NNNNNNNNNN NNNNNNNNNN NNNNNNNNNN       2418

NNNNNNNNNN NNNNNNNNNN NNNNNNNNNN NNNNNNNNNN NNNNNNNNNN NNNNNNNNNN       2478

NNNNNNNNNN NNNNNNNNNN NNNNNNNNNN NNNNNNNNNN NNNNNNNNNN NNNNNNNNNN       2538

NNNNNNNNNN NNNNNNNNNN NNNNNNNNNN NNNNNNNNNN NNNNNNNNNN NNNNNNNNNN       2598

NNNNNNNNNN NNNNNNNNNN NNNNNNNNNN NNNNNNNNNN NNNNNNNNNN NNNNNNNNNN       2658

NNNNNNNNNN NNNNNNNNNN NNNNNNNNNN NNNNNNNNNN NNNNNNNNNN NNNNNNNNNN       2718

NNNNNNNNNN NNNNNNNNNN NNNNNNNNNN NNNNNNNNNN NNNNNNNNNN NNNNNNNNNN       2778

NNNNNNNNNN NNNNNNNNNN NNNNNNNNNN NNNNNNNNNN NNNNNNNNNN NNNNNNNNNN       2838

NNNNNNNNNN NNNNNNNNNN NNNNNNNNNN NNNNNNNNNN NNNNNNNNNN NNNNNNNNNN       2898

NNNNNNNNNN NNNNNNNNNC CTGACTGAAC TTCTTACTGC CAAAGTTAAA TTCCATACCA       2958

ATGAGTTATT CTCTATTCTC TCTGTATTGA CATTTCATCT GCGGTATCCT TTAGGGTACA       3018

ATATTCCAAG TTTCTTTAGA CAAACGCAGG AACAAATGTT CACATATTTC TGTTTCTTTA       3078

TTCCTTTGAC AAGTAGGCGA GCATTTTAGC CTATGTTGGT CTCAAAAAAA ATCTTTTAAA       3138

TATGTTCCAG GTTCTTTAAT GGGACCTTTC AGGAGCAAAA GTCCTCCCAG GTTTGGTCAA       3198

TGTTCACCCT CNGTGGCCAT TGAGGAAAAT GCCCNNNNNG TTCTAGAGAT TGTTCTCACT       3258

TCTCAGGCTA AGGCCCATTG AGCAATGCCA GAAAGCATGC CTTATACTAG CAGTCAATTT       3318

GGAAGTTTGT AGTTTGTGTC TTTAGCATAG GTTATCAAAT AAATTTTATA TTTNCTTTTA       3378

AAAAAATCTC AACATTACTA AAATACAAAT ATCCTTTTAT TTTTCTTTGC AGAATTATCG       3438

GGGAACAAAT CCAGAAAATT TGTGTAAATT TCGGGTAGTT GCTCCACTTG ATACACAGTA       3498

TTTCTGCATA TTGTAATTTC TATGAAGATC TAGGTTGCAT TTCCCATACA TTCAAGCAGT       3558

TTCCATTGCA TTTTTATGAA TAAGATGACG CATACTGGGA AGTAAGGCAA ATACACTAAA       3618

AGGAATATGT GTTTGTATTC TGTATAGTTA TTACTCTTAA AAAAAGTAGT TGTAATTCAT       3678

CCACTCTTTT TACTTTCAAC TTTTTGCTAT TAAAAAATCA TTTTTAAATT TCAGTATTAA       3738

AGCAGAAACA TTTAAATTTA TTAGACCAGA AAAATAACAG ATTCTAGAAC TATAATTTGA       3798

ATCCATTTAA GCCCATAGCT AGAGCTAGAG ATTTTCACTA TTGGATCC                   3846

(2) INFORMATION FOR SEQ ID NO:6:

(i) SEQUENCE CHARACTERISTICS:
         (A) LENGTH: 266 amino acids
         (B) TYPE: amino acid
         (D) TOPOLOGY: linear (ii) MOLECULE TYPE: protein (xi) SEQUENCE DESCRIPTION: SEQ ID NO:6:

Gly Lys Tyr Ile Thr Phe Ile Pro Gly Pro Phe Gln Tyr Gln Leu Val
  1               5                  10                  15

Ile Lys Asn His Lys Gln Leu Ser Phe Arg Val Ser Ser Asn Lys Leu
                 20                  25                  30

Ser Glu Lys Ala Phe Ser Ile Ser Gln Leu Gln Lys Asn His Asp Met
             35                  40                  45

Asn Asp Glu Leu His Leu Cys Tyr Gln Phe Leu Gln Gly Lys Ser Leu
         50                  55                  60
```

-continued

```
Asp Ile Leu Leu Glu Ser Met Met Gln Asn Leu Lys Gln Val Phe Glu
 65                  70                  75                  80

Pro Gln Leu Leu Lys Thr Thr Ser Trp Asp Thr Ala Glu Leu Tyr Pro
                 85                  90                  95

Phe Cys Ser Ser Ile Ile Phe Glu Ile Thr Phe Thr Thr Ile Tyr Gly
            100                 105                 110

Lys Val Ile Val Cys Asp Asn Asn Lys Phe Ile Ser Glu Leu Arg Asp
        115                 120                 125

Asp Phe Leu Lys Phe Asp Asp Lys Phe Ala Tyr Leu Val Ser Asn Ile
    130                 135                 140

Pro Ile Glu Leu Leu Gly Asn Val Lys Ser Ile Arg Glu Lys Ile Ile
145                 150                 155                 160

Lys Cys Phe Ser Ser Glu Lys Leu Ala Lys Met Gln Gly Trp Ser Glu
                165                 170                 175

Val Phe Gln Ser Arg Gln Asp Asp Leu Glu Lys Tyr Tyr Val His Glu
            180                 185                 190

Asp Leu Glu Ile Gly Ala His His Leu Gly Phe Leu Trp Ala Ser Val
        195                 200                 205

Ala Asn Thr Ile Pro Thr Met Phe Trp Ala Thr Tyr Tyr Leu Leu Arg
    210                 215                 220

His Pro Glu Ala Met Ala Ala Val Arg Asp Glu Ile Asp Arg Leu Leu
225                 230                 235                 240

Gln Ser Thr Gly Gln Lys Glu Gly Ser Gly Phe Pro Ile His Leu Thr
                245                 250                 255

Arg Glu Gln Leu Asp Ser Leu Ile Cys Leu
            260                 265
```

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CAATTCGCGG CCGCTTTTTT TTTTTTTTT                     29

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CGACAGCAAC GG                                                     12

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

AATTCCGTTG CTGTCG                                                                  16

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Phe Xaa Xaa Gly Xaa Xaa Xaa Cys Xaa Gly Xaa Xaa Xaa Ala
1               5                   10

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GATCGCGGCC GC                                                                      12

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GGCCCTCGAG CCACCATGCA GGGGAGCCAC G                                                 31

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GGCCGAATTC TCAGCTTCTC CAAGAA                                                       26

(2) INFORMATION FOR SEQ ID NO:14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GACAGGTTTT GTGACCCAAA ACAAACTGGA TGGATCGCAA TC                                     42

(2) INFORMATION FOR SEQ ID NO:15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
ATCACGGAGC TCAGCACATG CAGCCTTACT CTGCAAAGCT TC                    42
```

(2) INFORMATION FOR SEQ ID NO:16:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

```
AGCCTTCTGG GTCGTAGCTG ACTCCTGCTG CTGAGCTGCA ACAGCTTT              48
```

(2) INFORMATION FOR SEQ ID NO:17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

```
TATATCCATA CCAACTTATT GGGAGTCCCA TCCTACCTCA TCAGC                 45
```

(2) INFORMATION FOR SEQ ID NO:18:

(i) SEQUENCE CHARACTERISTICS:
        (A) LENGTH: 506 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

```
Met Met Thr Thr Ser Leu Ile Trp Gly Ile Ala Ile Ala Ala Cys Cys
1               5                  10                  15

Cys Leu Trp Leu Ile Leu Gly Ile Arg Arg Arg Gln Thr Gly Glu Pro
            20                  25                  30

Pro Leu Glu Asn Gly Leu Gly Leu Ile Pro Tyr Leu Gly Cys Ala Leu
        35                  40                  45

Gln Phe Gly Ala Asn Pro Leu Glu Phe Leu Arg Ala Asn Gln Arg Lys
    50                  55                  60

His Gly His Val Phe Thr Cys Lys Leu Met Gly Lys Tyr Val His Phe
65                  70                  75                  80

Ile Thr Asn Pro Leu Ser Tyr His Lys Val Leu Cys His Gly Lys Tyr
                85                  90                  95

Phe Asp Trp Lys Lys Phe His Phe Ala Thr Ser Ala Lys Ala Phe Gly
            100                 105                 110

His Arg Ser Ile Asp Pro Met Asp Gly Asn Thr Thr Glu Asn Ile Asn
```

|     |     | 115 |     |     |     | 120 |     |     |     | 125 |     |
| --- | --- | --- | --- | --- | --- | --- | --- | --- | --- | --- | --- |

Asp Thr Phe Ile Lys Thr Leu Gln Gly His Ala Leu Asn Ser Leu Thr
    130                              135                  140

Glu Ser Met Met Glu Asn Leu Gln Arg Ile Met Arg Pro Pro Val Ser
145                  150                  155                  160

Ser Asn Ser Lys Thr Ala Ala Trp Val Thr Glu Gly Met Tyr Ser Phe
                165                  170                175

Cys Tyr Arg Val Met Phe Glu Ala Gly Tyr Leu Thr Ile Phe Gly Arg
            180                  185                190

Asp Leu Thr Arg Arg Asp Thr Gln Lys Ala His Ile Leu Asn Asn Leu
        195                  200              205

Asp Asn Phe Lys Gln Phe Asp Lys Val Phe Pro Ala Leu Val Ala Gly
210                  215                  220

Leu Pro Ile His Met Phe Arg Thr Ala His Asn Ala Arg Glu Lys Leu
225                  230                  235                240

Ala Glu Ser Leu Arg His Glu Asn Leu Gln Lys Arg Glu Ser Ile Ser
            245                  250                255

Glu Leu Ile Ser Leu Arg Met Phe Leu Asn Asp Thr Leu Ser Thr Phe
        260                  265              270

Asp Asp Leu Glu Lys Ala Lys Thr His Leu Val Val Leu Trp Ala Ser
    275                  280              285

Gln Ala Asn Thr Ile Pro Ala Thr Phe Trp Ser Leu Phe Gln Met Ile
290                  295                300

Arg Asn Pro Glu Ala Met Lys Ala Ala Thr Glu Glu Val Lys Arg Thr
305                  310                315              320

Leu Glu Asn Ala Gly Gln Lys Val Ser Leu Glu Gly Asn Pro Ile Cys
            325                  330              335

Leu Ser Gln Ala Glu Leu Asn Asp Leu Pro Val Leu Asn Ser Ile Ile
        340                  345              350

Lys Glu Ser Leu Arg Leu Ser Ser Ala Ser Leu Asn Ile Arg Thr Ala
    355                  360              365

Lys Glu Asp Phe Thr Leu His Leu Glu Asp Gly Ser Tyr Asn Ile Arg
370                  375                380

Lys Asp Ser Ile Ile Ala Leu Tyr Pro Gln Leu Met His Leu Asp Pro
385                  390                395              400

Glu Ile Tyr Pro Asp Pro Leu Thr Phe Lys Tyr Asp Arg Tyr Leu Asp
            405                  410              415

Glu Asn Gly Lys Thr Lys Thr Thr Phe Tyr Cys Asn Gly Leu Lys Leu
        420                  425              430

Lys Tyr Tyr Tyr Met Pro Phe Gly Ser Gly Ala Thr Ile Cys Pro Gly
            435                  440              445

Arg Leu Phe Ala Ile His Glu Ile Lys Gln Phe Leu Ile Leu Met Leu
450                  455                460

Ser Tyr Phe Glu Leu Glu Leu Ile Glu Gly Gln Ala Lys Cys Pro Pro
465                  470                475              480

Leu Asp Gln Ser Arg Ala Gly Leu Gly Ile Leu Pro Pro Leu Asn Asp
            485                  490              495

Ile Glu Phe Lys Tyr Lys Phe Lys His Leu
        500                  505

(2) INFORMATION FOR SEQ ID NO:19:

(i) SEQUENCE CHARACTERISTICS:
        (A) LENGTH: 14 amino acids
        (B) TYPE: amino acid (C) STRANDEDNESS:
            (D) TOPOLOGY: linear (ii) MOLECULE TYPE: peptide (xi) SEQUENCE DESCRIPTION: SEQ ID NO:19:

Phe Gly Leu Gly Thr Ser Lys Cys Pro Gly Arg Tyr Phe Ala
1               5                   10

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Phe Gly Ser Gly Ala Thr Ile Cys Pro Gly Arg Leu Phe Ala
1               5                   10

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Phe Gly Ala Gly Pro Arg Ser Cys Val Gly Glu Met Leu Ala
1               5                   10

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Phe Gly Phe Gly Met Arg Gln Cys Leu Gly Arg Arg Leu Ala
1               5                   10

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Phe Gly Cys Gly Ala Arg Val Cys Leu Gly Glu Pro Val Ala
1               5                   10

(2) INFORMATION FOR SEQ ID NO:24:

(i) SEQUENCE CHARACTERISTICS:
        (A) LENGTH: 14 amino acids
        (B) TYPE: amino acid

```
            (C) STRANDEDNESS:
            (D) TOPOLOGY: linear (ii) MOLECULE TYPE: peptide (xi) SEQUENCE DESCRIPTION: SEQ ID NO:24:

Phe Gly Trp Gly Val Arg Gln Cys Leu Gly Arg Arg Ile Ala
1               5                   10

(2) INFORMATION FOR SEQ ID NO:25:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:25:

Phe Gly Tyr Gly Val Arg Ala Cys Leu Gly Arg Arg Ile Ala
1               5                   10

(2) INFORMATION FOR SEQ ID NO:26:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:26:

Val Cys Leu Glu Ser Thr Ile Leu Glu Val Leu Arg Leu Cys Ser
1               5                   10                  15

(2) INFORMATION FOR SEQ ID NO:27:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:27:

Pro Val Leu Asn Ser Ile Ile Lys Glu Ser Leu Arg Leu Ser Ser
1               5                   10                  15

(2) INFORMATION FOR SEQ ID NO:28:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:28:

Val Leu Leu Glu His Thr Ile Arg Glu Val Leu Arg Ile Arg Pro
1               5                   10                  15

(2) INFORMATION FOR SEQ ID NO:29:

(i) SEQUENCE CHARACTERISTICS:
            (A) LENGTH: 15 amino acids
            (B) TYPE: amino acid
```

(C) STRANDEDNESS:
        (D) TOPOLOGY: linear (ii) MOLECULE TYPE: peptide (xi) SEQUENCE DESCRIPTION: SEQ ID NO:29:

Pro Leu Leu Arg Ala Ala Leu Lys Glu Thr Leu Arg Leu Tyr Pro
1               5                   10                  15

(2) INFORMATION FOR SEQ ID NO:30:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

Pro Leu Leu Asn Ala Thr Ile Ala Glu Val Leu Arg Leu Pro Val
1               5                   10                  15

(2) INFORMATION FOR SEQ ID NO:31:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Pro Leu Leu Lys Ala Ser Ile Lys Glu Thr Leu Arg Leu His Pro
1               5                   10                  15

(2) INFORMATION FOR SEQ ID NO:32:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Pro Leu Leu Lys Ala Val Leu Lys Glu Thr Leu Arg Leu Tyr Pro
1               5                   10                  15

(2) INFORMATION FOR SEQ ID NO:33:

(i) SEQUENCE CHARACTERISTICS:
        (A) LENGTH: 266 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:33:

Gly Lys Tyr Ile Thr Phe Val Leu Asn Pro Phe Gln Tyr Gln Tyr Val
1               5                   10                  15

Thr Lys Asn Pro Lys Gln Leu Ser Phe Gln Lys Phe Ser Ser Arg Leu
                20                  25                  30

Ser Ala Lys Ala Phe Ser Val Lys Lys Leu Leu Thr Asp Asp Asp Leu
                35                  40                  45

```
Asn Glu Asp Val His Arg Ala Tyr Leu Leu Leu Gln Gly Lys Pro Leu
 50                  55                  60

Asp Ala Leu Leu Glu Thr Met Ile Gln Glu Val Lys Glu Leu Phe Glu
 65                  70                  75                  80

Ser Gln Leu Leu Lys Ile Thr Asp Trp Asn Thr Glu Arg Ile Phe Ala
                 85                  90                  95

Phe Cys Gly Ser Leu Val Phe Glu Ile Thr Phe Ala Thr Leu Tyr Gly
                100                 105                 110

Lys Ile Leu Ala Gly Asn Lys Lys Gln Ile Ile Ser Glu Leu Arg Asp
                115                 120                 125

Asp Phe Phe Lys Phe Asp Asp Met Phe Pro Tyr Leu Val Ser Asp Ile
                130                 135                 140

Pro Ile Gln Leu Leu Arg Asn Glu Glu Ser Met Gln Lys Lys Ile Ile
145                 150                 155                 160

Lys Cys Leu Thr Ser Glu Lys Val Ala Gln Met Gln Gly Gln Ser Lys
                165                 170                 175

Ile Val Gln Glu Ser Gln Asp Leu Leu Lys Arg Tyr Tyr Arg His Asp
                180                 185                 190

Asp Ser Glu Ile Gly Ala His His Leu Gly Phe Leu Trp Ala Ser Leu
                195                 200                 205

Ala Asn Thr Ile Pro Ala Met Phe Trp Ala Met Tyr Tyr Ile Leu Arg
210                 215                 220

His Pro Glu Ala Met Glu Ala Leu Arg Asp Glu Ile Asp Ser Phe Leu
225                 230                 235                 240

Gln Ser Thr Gly Gln Lys Lys Gly Pro Gly Ile Ser Val His Phe Thr
                245                 250                 255

Arg Glu Gln Leu Asp Ser Leu Val Cys Leu
                260                 265

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

CTCCAGCCAT GGTCCTCG                                                 18

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GTCTCGCCAT GCTGCTCC                                                 18

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:36:

CAGCCACCAT GTGGGAGC                                                          18

(2) INFORMATION FOR SEQ ID NO:37:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:37:

TCGTCGGGAT GCAGGGAG                                                          18

(2) INFORMATION FOR SEQ ID NO:38:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:38:

TTTGCAAAAT GATGACCA                                                          18

(2) INFORMATION FOR SEQ ID NO:39:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:39:

TTTGCAAAAT GATGACTA                                                          18

(2) INFORMATION FOR SEQ ID NO:40:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:40:

TTTGCAAAAT GATGAGCA                                                          18

(2) INFORMATION FOR SEQ ID NO:41:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:41:

TCGGATCCAT GGCTGCGC                                              18

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

CACGATCTAT GGCTGTGT                                              18

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

TCGCCACCAT GCAGGGAG                                              18

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

GGCCCTCGAG CCACCATGCA GGGAGCCACG                                 30

(2) INFORMATION FOR SEQ ID NO:45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

GGCCGAATTC TCAGCTTCTC CAAGA                                      25